(12) United States Patent
Inouye et al.

(10) Patent No.: US 7,888,087 B2
(45) Date of Patent: Feb. 15, 2011

(54) FUSION PROTEIN OF FC-BINDING DOMAIN AND CALCIUM-BINDING PHOTOPROTEIN, GENE ENCODING THE SAME AND USE THEREOF

(75) Inventors: Satoshi Inouye, Yokohama (JP); Yuiko Sahara, Yokohama (JP); Junichi Sato, Yokohama (JP)

(73) Assignee: Chisso Corporation, Osaka (JP)

( * ) Notice: Subject to any disclaimer, the term of this patent is extended or adjusted under 35 U.S.C. 154(b) by 74 days.

(21) Appl. No.: 11/892,294

(22) Filed: Aug. 21, 2007

(65) Prior Publication Data

US 2008/0193980 A1 Aug. 14, 2008

(30) Foreign Application Priority Data

Aug. 22, 2006 (JP) .............................. 2006-224794

(51) Int. Cl.
*C12N 9/00* (2006.01)
*C12N 9/02* (2006.01)
*C12N 1/20* (2006.01)
*C12N 15/00* (2006.01)
*C12Q 1/00* (2006.01)
*C12Q 1/68* (2006.01)
*C12P 21/04* (2006.01)
*C07H 21/04* (2006.01)
*C07K 1/00* (2006.01)

(52) U.S. Cl. .................... 435/183; 435/189; 435/4; 435/6; 435/252.3; 435/320.1; 435/69.7; 435/7.1; 435/440; 435/69.1; 435/71.1; 536/23.2; 536/23.4; 530/350

(58) Field of Classification Search ........................ None
See application file for complete search history.

(56) References Cited

U.S. PATENT DOCUMENTS 5,550,213 A * 8/1996 Anderson et al. ............ 530/324

FOREIGN PATENT DOCUMENTS

EP 0 372 352 6/1990

OTHER PUBLICATIONS

Branden et al. Introduction to Protein Structure, Garland Publishing Inc., New York, p. 247, 1991.*
Nilson et al.—GenBank Acession No. AAA56730.1—1994.*
United Kingdom Search Report dated Dec. 20, 2007 relating to GB 07 16 137.5.
Biochemical and Biophysical Research Communications, vol. 171, 1990, Zenno, S. et al., "Bioluminescent Immunoassay Using a Fusion Protein of Protein A and the Photoprotein Aequorin," pp. 169-174.
Biochemical and Biophysical Research Communications, vol. 219, 1996, Frank, L. A. et al., "Use of proZZ-obelin Fusion Protein in Bioluminescent Immunoassay," pp. 475-479.
S. Inouye et al., *Cloning and Sequence Analysis of cDNA for the Luminescent Protein Aequorin*, Proc. Natl. Acad. Sci. USA, vol. 82, pp. 3154-3158, 1985.
J. F. Head et al., *The Crystal Structure of the Photoprotein Aequorin at 2.3 Å Resolution*, Nature, vol. 405, pp. 372-376, 2000.
S. Zenno et al., *Bioluminescent Immunoassay Usinq a Fusion Protein of Protein A and the Photoprotein Aequorin*, Biochemical and Biophysical Research Communications, vol. 171, No. 1, pp. 169-174, 1990.
B. Nilsson et al., *A Synthetic IgG-Binding Domain Based on Staphylococcal Protein A*, Protein Engineering, vol. 1, No. 2, pp. 107-113, 1987.
L. A. Frank et al., *Use of proZZ-Obelin Fusion Protein in Bioluminescent Immunoassay*, Biochemical and Biophysical Research Communications, vol. 219, No. 0258, pp. 475-479, 1996.

* cited by examiner

*Primary Examiner*—Yong D Pak
(74) *Attorney, Agent, or Firm*—Hogan Lovells US LLP

(57) ABSTRACT

The invention provides a calcium-binding photoprotein which has a high ability to bind to IgG and is capable of more sensitively detecting IgG. A fusion protein of the present invention composed of a ZZ domain having the ability to bind to the Fc region of IgG and the calcium-binding photoprotein apoaequorin is used for the detection and assay of calcium ions and the detection of IgG.

18 Claims, 4 Drawing Sheets cspA: cold shock protein A
TEE: translation enhancing element

SEQUENCE LISTING

```
<160> NUMBER OF SEQ ID NOS: 10

<210> SEQ ID NO 1
<211> LENGTH: 116
<212> TYPE: PRT
<213> ORGANISM: Artificial
<220> FEATURE:
<223> OTHER INFORMATION: Synthetic Construct

<400> SEQUENCE: 1

Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Ala Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys Val Asp Asn Lys Phe Asn Lys
    50                  55                  60

Glu Gln Gln Asn Ala Phe Tyr Glu Ile Leu His Leu Pro Asn Leu Asn
65                  70                  75                  80

Glu Glu Gln Arg Asn Ala Phe Ile Gln Ser Leu Lys Asp Asp Pro Ser
                85                  90                  95

Gln Ser Ala Asn Leu Leu Ala Glu Ala Lys Lys Leu Asn Asp Ala Gln
            100                 105                 110

Ala Pro Lys Val
        115

<210> SEQ ID NO 2
<211> LENGTH: 348
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(348)

<400> SEQUENCE: 2 gac aac aaa ttc aac aaa gaa caa caa aac gcg ttc tat gag atc tta      48
Asp Asn Lys Phe Asn Lys Glu Gln Gln Asn Ala Phe Tyr Glu Ile Leu
1               5                   10                  15 cat tta cct aac tta aac gaa gaa caa cga aac gcc ttc atc caa agt      96
His Leu Pro Asn Leu Asn Glu Glu Gln Arg Asn Ala Phe Ile Gln Ser
            20                  25                  30 tta aaa gat gac cca agc caa agc gct aac ctt tta gca gaa gct aaa     144
Leu Lys Asp Asp Pro Ser Gln Ser Ala Asn Leu Leu Ala Glu Ala Lys
        35                  40                  45 aag cta aat gat gct cag gcg ccg aaa gta gac aac aaa ttc aac aaa     192
Lys Leu Asn Asp Ala Gln Ala Pro Lys Val Asp Asn Lys Phe Asn Lys
    50                  55                  60 gaa caa caa aac gcg ttc tat gag atc tta cat tta cct aac tta aac     240
```

```
Glu Gln Gln Asn Ala Phe Tyr Glu Ile Leu His Leu Pro Asn Leu Asn
65                  70                  75                  80 gaa gaa caa cga aac gcc ttc atc caa agt tta aaa gat gac cca agc      288
Glu Glu Gln Arg Asn Ala Phe Ile Gln Ser Leu Lys Asp Asp Pro Ser
                85                  90                  95 caa agc gct aac ctt tta gca gaa gct aaa aag cta aat gat gct cag      336
Gln Ser Ala Asn Leu Leu Ala Glu Ala Lys Lys Leu Asn Asp Ala Gln
            100                 105                 110 gcg ccg aaa gta                                                      348
Ala Pro Lys Val
            115

<210> SEQ ID NO 3
<211> LENGTH: 188
<212> TYPE: PRT
<213> ORGANISM: Aequorea victoria

<400> SEQUENCE: 3

Lys Leu Thr Ser Asp Phe Asp Asn Pro Arg Trp Ile Gly Arg His Lys
1               5                   10                  15

His Met Phe Asn Phe Leu Asp Val Asn His Asn Gly Lys Ile Ser Leu
                20                  25                  30

Asp Glu Met Val Tyr Lys Ala Ser Asp Ile Val Ile Asn Asn Leu Gly
            35                  40                  45

Ala Thr Pro Glu Gln Ala Lys Arg His Lys Asp Ala Val Glu Ala Phe
        50                  55                  60

Phe Gly Gly Ala Gly Met Lys Tyr Gly Val Glu Thr Asp Trp Pro Ala
65                  70                  75                  80

Tyr Ile Glu Gly Trp Lys Lys Leu Ala Thr Asp Glu Leu Glu Lys Tyr
                85                  90                  95

Ala Lys Asn Glu Pro Thr Leu Ile Arg Ile Trp Gly Asp Ala Leu Phe
            100                 105                 110

Asn Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
130                 135                 140

Glu Glu Thr Phe Arg Val Cys Asp Ile Asp Glu Ser Gly Gln Leu Asp
145                 150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185

<210> SEQ ID NO 4
<211> LENGTH: 564
<212> TYPE: DNA
<213> ORGANISM: Aequorea victoria
<220> FEATURE:
<221> NAME/KEY: CDS
<222> LOCATION: (1)..(564)

<400> SEQUENCE: 4 aaa ctt aca tca gac ttc gac aac cca aga tgg att gga cga cac aag       48
Lys Leu Thr Ser Asp Phe Asp Asn Pro Arg Trp Ile Gly Arg His Lys
1               5                   10                  15 cac atg ttc aat ttc ctt gat gtc aac cac aat gga aaa atc tct ctt       96
His Met Phe Asn Phe Leu Asp Val Asn His Asn Gly Lys Ile Ser Leu
                20                  25                  30 gac gag atg gtc tac aag gca tct gat att gtc atc aat aac ctt gga      144
```

```
                Asp Glu Met Val Tyr Lys Ala Ser Asp Ile Val Ile Asn Asn Leu Gly
                         35                  40                  45 gca aca cct gag caa gcc aaa cga cac aaa gat gct gta gaa gcc ttc              192
Ala Thr Pro Glu Gln Ala Lys Arg His Lys Asp Ala Val Glu Ala Phe
 50                  55                  60 ttc gga gga gct gga atg aaa tat ggt gtg gaa act gat tgg cct gca              240
Phe Gly Gly Ala Gly Met Lys Tyr Gly Val Glu Thr Asp Trp Pro Ala
 65                  70                  75                  80 tat att gaa gga tgg aaa aaa ttg gct act gat gaa ttg gag aaa tac              288
Tyr Ile Glu Gly Trp Lys Lys Leu Ala Thr Asp Glu Leu Glu Lys Tyr
             85                  90                  95 gcc aaa aac gaa cca acg ctc atc cgt ata tgg ggt gat gct ttg ttt              336
Ala Lys Asn Glu Pro Thr Leu Ile Arg Ile Trp Gly Asp Ala Leu Phe
            100                 105                 110 aat atc gtt gac aaa gat caa aat gga gcc att aca ctg gat gaa tgg              384
Asn Ile Val Asp Lys Asp Gln Asn Gly Ala Ile Thr Leu Asp Glu Trp
            115                 120                 125 aaa gca tac acc aaa gct gct ggt atc atc caa tca tca gaa gat tgc              432
Lys Ala Tyr Thr Lys Ala Ala Gly Ile Ile Gln Ser Ser Glu Asp Cys
130                 135                 140 gag gaa aca ttc aga gtg tgc gat att gat gaa agt gga caa ctc gat              480
Glu Glu Thr Phe Arg Val Cys Asp Ile Asp Glu Ser Gly Gln Leu Asp
145                 150                 155                 160 gtt gat gag atg aca aga caa cat tta gga ttt tgg tac act atg gac              528
Val Asp Glu Met Thr Arg Gln His Leu Gly Phe Trp Tyr Thr Met Asp
                165                 170                 175 cct gct tgc gaa aag ctc tac ggt gga gct gtc ccc                              564
Pro Ala Cys Glu Lys Leu Tyr Gly Gly Ala Val Pro
            180                 185

<210> SEQ ID NO 5
<211> LENGTH: 334
<212> TYPE: PRT
<213> ORGANISM: Artificial
<220> FEATURE:
<223> OTHER INFORMATION: Synthetic Construct

<400> SEQUENCE: 5

Met Asn His Lys Val His His His His His His Met Ala Gln His Asp
 1               5                  10                  15

Glu Ala Val Asp Asn Lys Phe Asn Lys Glu Gln Gln Asn Ala Phe Tyr
                 20                  25                  30

Glu Ile Leu His Leu Pro Asn Leu Asn Glu Glu Gln Arg Asn Ala Phe
             35                  40                  45

Ile Gln Ser Leu Lys Asp Asp Pro Ser Gln Ser Ala Asn Leu Leu Ala
         50                  55                  60

Glu Ala Lys Lys Leu Asn Asp Ala Gln Ala Pro Lys Val Asp Asn Lys
 65                  70                  75                  80

Phe Asn Lys Glu Gln Gln Asn Ala Phe Tyr Glu Ile Leu His Leu Pro
                 85                  90                  95

Asn Leu Asn Glu Glu Gln Arg Asn Ala Phe Ile Gln Ser Leu Lys Asp
            100                 105                 110

Asp Pro Ser Gln Ser Ala Asn Leu Leu Ala Glu Ala Lys Lys Leu Asn
        115                 120                 125

Asp Ala Gln Ala Pro Lys Val Asp Ala Asn Ser Ser Ser Gly Ser Glu
    130                 135                 140

Phe Met Lys Leu Thr Ser Asp Phe Asp Asn Pro Arg Trp Ile Gly Arg
145                 150                 155                 160
```

```
His Lys His Met Phe Asn Phe Leu Asp Val Asn His Asn Gly Lys Ile
            165                 170                 175

Ser Leu Asp Glu Met Val Tyr Lys Ala Ser Asp Ile Val Ile Asn Asn
            180                 185                 190

Leu Gly Ala Thr Pro Glu Gln Ala Lys Arg His Lys Asp Ala Val Glu
            195                 200                 205

Ala Phe Phe Gly Gly Ala Gly Met Lys Tyr Gly Val Glu Thr Asp Trp
            210                 215                 220

Pro Ala Tyr Ile Glu Gly Trp Lys Lys Leu Ala Thr Asp Glu Leu Glu
225                 230                 235                 240

Lys Tyr Ala Lys Asn Glu Pro Thr Leu Ile Arg Ile Trp Gly Asp Ala
            245                 250                 255

Leu Phe Asn Ile Val Asp Lys Asp Gln Asn Gly Ala Ile Thr Leu Asp
            260                 265                 270

Glu Trp Lys Ala Tyr Thr Lys Ala Ala Gly Ile Ile Gln Ser Ser Glu
            275                 280                 285

Asp Cys Glu Glu Thr Phe Arg Val Cys Asp Ile Asp Glu Ser Gly Gln
            290                 295                 300

Leu Asp Val Asp Glu Met Thr Arg Gln His Leu Gly Phe Trp Tyr Thr
305                 310                 315                 320

Met Asp Pro Ala Cys Glu Lys Leu Tyr Gly Gly Ala Val Pro
            325                 330

<210> SEQ ID NO 6
<211> LENGTH: 1005
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(1005)

<400> SEQUENCE: 6 atg aat cac aaa gtg cat cat cat cat cat cat atg gcg caa cac gat      48
Met Asn His Lys Val His His His His His His Met Ala Gln His Asp
1               5                   10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
                20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
            35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
        50                  55                  60 gaa gct aaa aag cta aat gat gct cag gcg ccg aaa gta gac aac aaa     240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct     288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat     336
Asn Leu Asn Glu Glu Gln Arg Asn Ala Phe Ile Gln Ser Leu Lys Asp
            100                 105                 110 gac cca agc caa agc gct aac ctt tta gca gaa gct aaa aag cta aat     384
Asp Pro Ser Gln Ser Ala Asn Leu Leu Ala Glu Ala Lys Lys Leu Asn
        115                 120                 125
```

```
gat gct cag gcg ccg aaa gta gac gca aat tcg agc tcg gga tcc gaa        432
Asp Ala Gln Ala Pro Lys Val Asp Ala Asn Ser Ser Ser Gly Ser Glu
    130                 135                 140 ttc atg aaa ctt aca tca gac ttc gac aac cca aga tgg att gga cga        480
Phe Met Lys Leu Thr Ser Asp Phe Asp Asn Pro Arg Trp Ile Gly Arg
145                 150                 155                 160 cac aag cac atg ttc aat ttc ctt gat gtc aac cac aat gga aaa atc        528
His Lys His Met Phe Asn Phe Leu Asp Val Asn His Asn Gly Lys Ile
                165                 170                 175 tct ctt gac gag atg gtc tac aag gca tct gat att gtc atc aat aac        576
Ser Leu Asp Glu Met Val Tyr Lys Ala Ser Asp Ile Val Ile Asn Asn
            180                 185                 190 ctt gga gca aca cct gag caa gcc aaa cga cac aaa gat gct gta gaa        624
Leu Gly Ala Thr Pro Glu Gln Ala Lys Arg His Lys Asp Ala Val Glu
        195                 200                 205 gcc ttc ttc gga gga gct gga atg aaa tat ggt gtg gaa act gat tgg        672
Ala Phe Phe Gly Gly Ala Gly Met Lys Tyr Gly Val Glu Thr Asp Trp
    210                 215                 220 cct gca tat att gaa gga tgg aaa aaa ttg gct act gat gaa ttg gag        720
Pro Ala Tyr Ile Glu Gly Trp Lys Lys Leu Ala Thr Asp Glu Leu Glu
225                 230                 235                 240 aaa tac gcc aaa aac gaa cca acg ctc atc cgt ata tgg ggt gat gct        768
Lys Tyr Ala Lys Asn Glu Pro Thr Leu Ile Arg Ile Trp Gly Asp Ala
                245                 250                 255 ttg ttt aat atc gtt gac aaa gat caa aat gga gcc att aca ctg gat        816
Leu Phe Asn Ile Val Asp Lys Asp Gln Asn Gly Ala Ile Thr Leu Asp
            260                 265                 270 gaa tgg aaa gca tac acc aaa gct gct ggt atc atc caa tca tca gaa        864
Glu Trp Lys Ala Tyr Thr Lys Ala Ala Gly Ile Ile Gln Ser Ser Glu
        275                 280                 285 gat tgc gag gaa aca ttc aga gtg tgc gat att gat gaa agt gga caa        912
Asp Cys Glu Glu Thr Phe Arg Val Cys Asp Ile Asp Glu Ser Gly Gln
    290                 295                 300 ctc gat gtt gat gag atg aca aga caa cat tta gga ttt tgg tac act        960
Leu Asp Val Asp Glu Met Thr Arg Gln His Leu Gly Phe Trp Tyr Thr
305                 310                 315                 320 atg gac cct gct tgc gaa aag ctc tac ggt gga gct gtc ccc taa           1005
Met Asp Pro Ala Cys Glu Lys Leu Tyr Gly Gly Ala Val Pro
                325                 330

<210> SEQ ID NO 7
<211> LENGTH: 36
<212> TYPE: DNA
<213> ORGANISM: Artificial
<220> FEATURE:
<223> OTHER INFORMATION: Primer

<400> SEQUENCE: 7
ccggaattca tgaaacttac atcagacttc gacaac                                36

<210> SEQ ID NO 8
<211> LENGTH: 36
<212> TYPE: DNA
<213> ORGANISM: Artificial
<220> FEATURE:
<223> OTHER INFORMATION: Primer

<400> SEQUENCE: 8
cgcgtcgact tagggacag ctccaccgta gagctt                                 36

<210> SEQ ID NO 9
<211> LENGTH: 30
```

```
<212> TYPE: DNA
<213> ORGANISM: Artificial
<220> FEATURE:
<223> OTHER INFORMATION: Primer

<400> SEQUENCE: 9
ccgcatatgg cgcaacacga tgaagccgtg                                    30

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
ggcggatccc gagctcgaat ttgcgtctac                                    30
```

US 7,888,087 B2

FUSION PROTEIN OF FC-BINDING DOMAIN AND CALCIUM-BINDING PHOTOPROTEIN, GENE ENCODING THE SAME AND USE THEREOF

CROSS REFERENCE TO RELATED APPLICATIONS

This application claims priority under 35 U.S.C. §119 to Japanese Patent Application No. JP 2006-224794, filed Aug. 22, 2006, which application is expressly incorporated herein by reference in its entirety.

BACKGROUND OF THE INVENTION

1. Field of the Invention

The invention relates to fusion proteins of Fc-binding domains and calcium-binding photoproteins, genes encoding the same, and use thereof. More specifically, the invention relates to fusion proteins of a ZZ domain having the ability to bind to the Fc region of immunoglobulin G (IgG) with the calcium-binding photoprotein apoaequorin, genes encoding the same and use thereof.

2. Related Art

Calcium-binding photoproteins are photoproteins in which an apoprotein and a peroxide of a light-emitting substrate exist in the state of a complex formed therefrom. Calcium-binding photoproteins have the property of emitting transient light on binding to a calcium ion.

Known calcium-binding photoproteins include aequorin, obelin, clytin, mitrocomin, mineopsin and bervoin. Of these, aequorin is a typical calcium-binding photoprotein, the higher-order structure and light-emitting mechanism of which have been reported in detail (see, for example, Inouye et al., *Proc. Natl. Acad. Sci. USA,* 82, 3154-3158 (1985); Head et al., *Nature,* 405, 372-376 (2000)). Since aequorin has a very high sensitivity to calcium ions, it is used to detect and assay trace amounts of calcium ions, and to measure changes in the intracellular concentration of calcium ions.

Aequorin exists in the state a complex formed from apoaequorin and a peroxide of the light-emitting substance coelenterazine. When aequorin bonds with a calcium ion, it momentarily emits light and forms coelenteramide, which is an oxide of coelenterazine, and carbon dioxide.

Protein A is a protein which originates in the cell wall of *Staphylococcus aureus*, and is known to bond specifically with the Fc region of IgG. It has been reported that a fusion protein of protein A and aequorin can be used in immunoassays. The minimum concentration of IgG that can be measured using a fusion protein of protein A and aequorin is 20 ng/mL per assay (see, for example, *Biochem. Biophys. Res. Commun.,* 171, 169-174 (1990)).

The ZZ domain is a synthetic IgG-binding region which was developed based on the IgG-binding region of protein A (see, for example, Nilsson, B. et al., *Protein Eng.,* 1, 107-113 (1987)). It has been reported that a fusion protein of the ZZ domain and the calcium-binding photoprotein obelin can be used in immunoassays. The minimum concentration of IgG that can be measured using a fusion protein of the ZZ domain and obelin is 10 ng/mL (see, for example, *Biochem. Biophys. Res. Commun.,* 219, 475-479 (1996)).

SUMMARY OF THE INVENTION

In this context, there exists a need for calcium-binding photoproteins which, compared with conventional fusion proteins, have a higher ability to bind to IgG and are capable of more sensitively detecting IgG.

It has been observed that fusion proteins of the ZZ domain capable of binding to the Fc region of IgG with the calcium-binding photoprotein aequorin can be efficiently produced, enabling IgG to be detected to a greater sensitivity (i.e., at a lower IgG detection limit) than known fusion proteins.

Accordingly, the invention includes:

[1] A fusion protein including (1) a first region selected from the group of:

(a) a region having the amino acid sequence set forth in SEQ ID NO: 1, (b) a region which has an amino acid sequence with, in the amino acid sequence of SEQ ID NO: 1, one or more deleted, substituted, inserted and/or added amino acids, and which has the ability to bind to the Fc region of IgG, (c) a region which has an amino acid sequence that is at least 70% identical to the amino acid sequence of SEQ ID NO: 1, and which has the ability to bind to the Fc region of IgG, and (d) a region which has an amino acid sequence encoded by a polynucleotide that hybridizes under stringent conditions to a polynucleotide having a nucleotide sequence complementary to the nucleotide sequence of SEQ ID NO: 2, and which has the ability to bind to the Fc region of IgG; and (2) a second region selected from the group of:

(e) a region having the amino acid sequence set forth in SEQ ID NO: 3, (f) a region which has an amino acid sequence with, in the amino acid sequence of SEQ ID NO: 3, one or more deleted, substituted, inserted and/or added amino acids, and which has the ability to bind to a peroxide of coelenterazine or a peroxide of a coelenterazine derivative so as to form a holoprotein that emits light under the action of a calcium ion, (g) a region which has an amino acid sequence that is at least 70% identical to the amino acid sequence of SEQ ID NO: 3, and which has the ability to bind to a peroxide of coelenterazine or a peroxide of a coelenterazine derivative so as to form a holoprotein that emits light under the action of a calcium ion, and (h) a region which has an amino acid sequence encoded by a polynucleotide that hybridizes under stringent conditions to a polynucleotide having a nucleotide sequence complementary to the nucleotide sequence of SEQ ID NO: 4, and which has the ability to bind to a peroxide of coelenterazine or a peroxide of a coelenterazine derivative so as to form a holoprotein that emits light under the action of a calcium ion.

[2] The fusion protein of [1] above, wherein (1) the first region is selected from the group of:

(a) a region having the amino acid sequence set forth in SEQ ID NO: 1, (b) a region which has an amino acid sequence with, in the amino acid sequence of SEQ ID NO: 1, from one to ten deleted, substituted, inserted and/or added amino acids, and which has the ability to bind to the Fc region of IgG, (c) a region which has an amino acid sequence that is at least 90% identical to the amino acid sequence of SEQ ID NO: 1, and which has the ability to bind to the Fc region of IgG, and (d) a region which has an amino acid sequence encoded by a polynucleotide that hybridizes under stringent conditions to a polynucleotide having a nucleotide sequence complementary to the nucleotide sequence of SEQ ID NO: 2, and which has the ability to bind to the Fc region of IgG; and (2) the second region is selected from the group of:

(e) a region having the amino acid sequence set forth in SEQ ID NO: 3, (f) a region which has an amino acid sequence with, in the amino acid sequence of SEQ ID NO: 3, from one to ten deleted, substituted, inserted and/or added amino acids, and which has the ability to bind to a peroxide of coelenterazine or a peroxide of a coelenterazine derivative so as to form a holoprotein that emits light under the action of a calcium ion, (g) a region which has an amino acid sequence that is at least 90% identical to the amino acid sequence of SEQ ID NO: 3, and which has the ability to bind to a peroxide of coelenterazine or a peroxide of a coelenterazine derivative so as to form a holoprotein that emits light under the action of a calcium ion, and (h) a region which has an amino acid sequence encoded by a polynucleotide that hybridizes under stringent conditions to a polynucleotide having a nucleotide sequence complementary to the nucleotide sequence of SEQ ID NO: 4, and which has the ability to bind to a peroxide of coelenterazine or a peroxide of a coelenterazine derivative so as to form a holoprotein that emits light under the action of a calcium ion.

[3] A fusion protein composed of:

(1) a region having a first amino acid sequence set forth in SEQ ID NO: 1, and (2) a region having a second amino acid sequence set forth in SEQ ID NO: 3.

[4] The fusion protein according to any one of [1] to [3] above, further including an amino acid sequence for enhancing translation and/or an amino acid sequence for purification.

[5] A fusion protein having the amino acid sequence set forth in SEQ ID NO: 5.

[6] A holoprotein including the fusion protein of any one of [1] to [5] above and a peroxide of coelenterazine or a peroxide of a coelenterazine derivative.

[7] A polynucleotide including a polynucleotide encoding the fusion protein of any one of [1] to [5] above.

[8] A polynucleotide composed of:

(1) a first coding sequence selected from the group of:

(a) a polynucleotide including a polynucleotide having the nucleotide sequence set forth in SEQ ID NO: 2, (b) a polynucleotide including a polynucleotide which hybridizes under stringent conditions to a polynucleotide having a nucleotide sequence complementary to the nucleotide sequence of SEQ ID NO: 2, and which encodes a region having the ability to bind to the Fc region of IgG, (c) a polynucleotide including a polynucleotide encoding a region having the amino acid sequence set forth in SEQ ID NO: 1, and (d) a polynucleotide including a polynucleotide encoding a region which has an amino acid sequence with, in the amino acid sequence of SEQ ID NO: 1, one or more deleted, substituted, inserted and/or added amino acids, and which has the ability to bind to the Fc region of IgG; and (2) a second coding sequence selected from the group of:

(e) a polynucleotide including a polynucleotide having the nucleotide sequence set forth in SEQ ID NO: 4, (f) a polynucleotide including a polynucleotide which hybridizes under stringent conditions to a polynucleotide having a nucleotide sequence complementary to the nucleotide sequence of SEQ ID NO: 4, and which encodes a region having the ability to bind to a peroxide of coelenterazine or a peroxide of a coelenterazine derivative so as to form a holoprotein that emits light under the action of a calcium ion, (g) a polynucleotide including a polynucleotide encoding a region having the amino acid sequence set forth in SEQ ID NO: 3, and (h) a polynucleotide including a polynucleotide encoding a region which has an amino acid sequence with, in the amino acid sequence of SEQ ID NO: 3, one or more deleted, substituted, inserted and/or added amino acids, and which encodes a region having the ability to bind to a peroxide of coelenterazine or a peroxide of a coelenterazine derivative so as to form a holoprotein that emits light under the action of a calcium ion.

[9] The polynucleotide of [8] above, wherein (1) the first coding sequence is selected from the group of:

(a) a polynucleotide including a polynucleotide having the nucleotide sequence set forth in SEQ ID NO: 2, (b) a polynucleotide including a polynucleotide which hybridizes under highly stringent conditions to a polynucleotide having a nucleotide sequence complementary to the nucleotide sequence of SEQ ID NO: 2, and which encodes a region having the ability to bind to the Fc region of IgG, (c) a polynucleotide including a polynucleotide encoding a region having the amino acid sequence set forth in SEQ ID NO: 1, and (d) a polynucleotide including a polynucleotide encoding a region which has an amino acid sequence with, in the amino acid sequence of SEQ ID NO: 1, from one to ten deleted, substituted, inserted and/or added amino acids, and which has the ability to bind to the Fc region of IgG; and (2) the second coding sequence is selected from the group of:

(e) a polynucleotide including a polynucleotide having the nucleotide sequence set forth in SEQ ID NO: 4, (f) a polynucleotide including a polynucleotide which hybridizes under highly stringent conditions to a polynucleotide having a nucleotide sequence complementary to the nucleotide sequence of SEQ ID NO: 4, and which encodes a region having the ability to bind to a peroxide of coelenterazine or a peroxide of a coelenterazine derivative so as to form a holoprotein that emits light under the action of a calcium ion, (g) a polynucleotide including a polynucleotide encoding a region having the amino acid sequence set forth in SEQ ID NO: 3, and (h) a polynucleotide including a polynucleotide encoding a region which has an amino acid sequence with, in the amino acid sequence of SEQ ID NO: 3, one to ten deleted, substituted, inserted and/or added amino acids, and which encodes a region having the ability to bind to a peroxide of coelenterazine or a peroxide of a coelenterazine derivative so as to form a holoprotein that emits light under the action of a calcium ion.

[10] A polynucleotide including a polynucleotide having the nucleotide sequence set forth in SEQ ID NO: 6.

[11] A recombinant vector which includes the polynucleotide of any one of [7] to [10] above.

[12] A transformant having inserted therein the recombinant vector of [11] above.

[13] A method for producing the fusion protein of any one of [1] to [5] above, which method includes the step of culturing the transformant of [12] above so as to induce the transformant to produce the fusion protein of any one of [1] to [5] above.

[14] A kit which includes the fusion protein of any one of [1] to [5] above or the holoprotein of [6] above.

[15] An immunoassay kit which includes the fusion protein of any one of [1] to [5] above or the holoprotein of [6] above.

[16] A method for detecting or assaying calcium ions, which method includes using the fusion protein of any one of [1] to [5] above or the holoprotein of [6] above.

[17] An immunoassay method which includes using the fusion protein of any one of [1] to [5] above or the holoprotein of [6] above.

By bringing the fusion protein of the invention into contact with the light-emitting substrate coelenterazine, a holoprotein that includes the inventive fusion protein and a peroxide of coelenterazine can easily be formed. The holoprotein of the invention exists as a complex which, in the presence of coelenterazine and oxygen, arises from the fusion protein of the invention and a peroxide of coelenterazine. The complex emits transient light when it binds to a calcium ion. The fusion protein of the invention can thus be advantageously used for detecting or measuring calcium ions.

Moreover, the fusion protein of the invention has a high IgG binding ability. As noted above, a holoprotein that includes the fusion protein of the invention and a peroxide of the light-emitting substrate coelenterazine is capable of emitting light under the action of calcium ions. The fusion protein and holoprotein of the invention can thus be advantageously used for detecting IgG.

By employing as the host a prokaryotic cell that is widely used as an expression system for recombinant proteins, the fusion protein of the invention can be expressed as a soluble protein in cytoplasm, thus enabling efficient production of the fusion protein.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DESCRIPTION OF THE PREFERRED EMBODIMENTS

Figure 1:
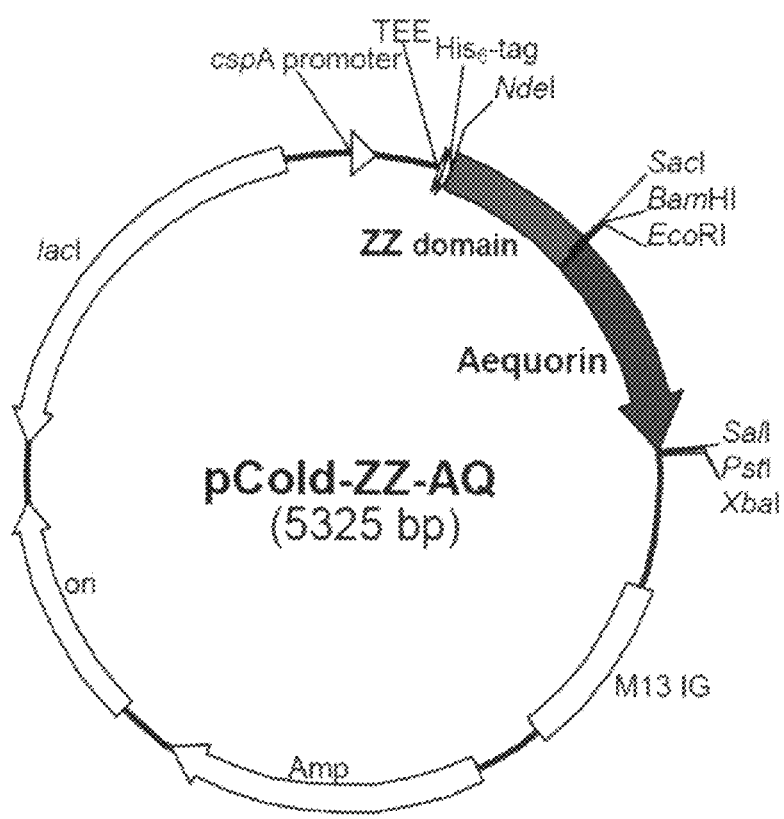
FIG. 1 is a schematic diagram showing the ZZ-apoaequorin expression vector p Cold-ZZ-AQ which may be used in the invention. The amino acid sequence of FIG. 1 is an abbreviated form of SEQ ID NO:5.

Embodiments of the invention are described in detail below.

1. Fusion Protein of the Invention

"Fusion protein of the invention" refers herein to a fusion protein that includes a first region selected from among regions having the amino acid sequence of SEQ ID NO: 1 and regions having a substantially similar activity or ability as regions having the amino acid sequence of SEQ ID NO: 1, and a second region selected from among regions having the amino acid sequence of SEQ ID NO: 3 and regions having a substantially similar activity or ability as regions having the amino acid sequence of SEQ ID NO: 3.

In this specification, the first region selected from among regions having the amino acid sequence of SEQ ID NO: 1 and regions having a substantially similar activity or ability as regions having the amino acid sequence of SEQ ID NO: 1 is sometimes referred to as the "ZZ domain." The second region selected from among regions having the amino acid sequence of SEQ ID NO: 3 and regions having a substantially similar activity or ability as regions having the amino acid sequence of SEQ ID NO: 3 is sometimes referred to as "apoaequorin" or "apoAQ."

The fusion protein of the invention may additionally include an amino acid sequence for enhancing translation and/or a peptide sequence for purification. Amino acid sequences for enhancing translation that may be used include peptide sequences employed in the technical field of the invention. An illustrative example of an amino acid sequence for enhancing translation is a TEE sequence. Peptide sequences for purification that may be used include peptide sequences employed in the technical field of the invention. Illustrative examples of peptide sequences for purification include histidine tag sequences having an amino acid sequence in which at least four, and preferably at least six, continuous histidine residues, and the amino acid sequence of the glutathione-binding domain in glutathione S-transferase.

The method for obtaining the fusion protein of the invention is not subject to any particular limitation. The fusion protein of the invention may be a fusion protein synthesized by chemical synthesis, or a recombinant fusion protein produced by a genetic engineering technique. If the fusion protein of the invention is to be chemically synthesized, synthesis may be carried out by, for example, the Fmoc (fluorenylmethyloxycarbonyl) process or the tBoc (t-butyloxycarbonyl) process. In addition, peptide synthesizers available from, for example, Advanced ChemTech, PerkinElmer, Pharmacia, Protein Technology Instrument, Syntheceh-Vega, PerSeptive and Shimadzu Corporation may be used for chemical synthesis. If the fusion protein of the invention is to be produced by a genetic engineering technique, production may be carried out using a conventional genetic recombination technique. More specifically, the fusion protein of the invention may be produced by inserting a polynucleotide (e.g., DNA) encoding the inventive fusion protein into a suitable expression system. The polynucleotide encoding the fusion protein of the invention and expression of the inventive fusion protein with an expression system are described later in the specification.

By bringing the fusion protein of the invention into contact with the light-emitting substrate coelenterazine or a derivative thereof (e.g., h-coelenterazine, e-coelenterazine, cl-coelenterazine, ch-coelenterazine, hep-coelenterazine) in the presence of oxygen, a holoprotein that includes the inventive fusion protein and a peroxide of coelenterazine or a peroxide of a coelenterazine derivative can be obtained. "Coelenterazine or a derivative thereof" is sometimes referred to simply as "coelenterazine" below. In the specification, the holoprotein that includes the inventive fusion protein and a peroxide of coelenterazine or a peroxide of a coelenterazine derivative is sometimes referred to simply as "the holoprotein of the invention" or as "ZZ-aequorin" or "ZZ-AQ." Also, holoproteins that include the fusion protein of the invention and a peroxide of coelenterazine or a peroxide of a coelenterazine derivative are sometimes referred to as "the photoprotein of the invention."

Examples of the holoprotein of the invention include (1) holoproteins that include the inventive fusion protein and a peroxide of coelenterazine, and (2) holoproteins that include the inventive fusion protein and a peroxide of a coelenterazine derivative. Holoproteins that include the inventive fusion protein and a peroxide of a coelenterazine derivative are exemplified by holoproteins that include the inventive fusion protein and the peroxide of h-coelenterazine, holoproteins that include the inventive fusion protein and the peroxide of e-coelenterazine, holoproteins that include the inventive fusion protein and the peroxide of cl-coelenterazine, holoproteins that include the inventive fusion protein and the peroxide of ch-coelenterazine, and holoproteins that include the inventive fusion protein and the peroxide of hcp-coelenterazine. The holoprotein of the invention may be produced from the fusion protein of the invention and coelenterazine in the same way as conventional calcium-binding photoproteins (e.g., aequorin). More specifically, the holoprotein of the invention may be produced by a method in general accordance with the preparation process described in, for example, *Biochem. J*, 261, 913-920 (1989). The holoprotein of the invention exists in the state of a complex (photoprotein of the invention) formed of the inventive fusion protein and a peroxide of coelenterazine. When a calcium ion binds to this complex (photoprotein of the invention), it emits transient luminescence. Consequently, coelenteramide (an oxide of coelenterazine) and carbon dioxide are formed.

First Region:

As used herein, "first region" refers to regions having the amino acid sequence set forth in SEQ ID NO: 1 and regions having a substantially similar activity or ability as regions having the amino acid sequence set forth in SEQ ID NO: 1.

"Substantially similar activity or ability as regions having the amino acid sequence set forth in SEQ ID NO: 1" refers to, for example, the activity or ability to bind to the Fc region of IgG. The activity or ability to bind to the Fc region of IgG can be measured by, for example, the Western blotting method or the methods described in the subsequent examples.

Examples of the first region include (a) regions having the amino acid sequence set forth in SEQ ID NO: 1, and (b) regions which have an amino acid sequence with, in the amino acid sequence of SEQ ID NO: 1, one or more deleted, substituted, inserted and/or added amino acids, and which have an activity or ability that is substantially similar to that of a region having the amino acid sequence of SEQ ID NO: 1.

In the specification, the range of "one or more" in the "amino acid sequence having one or more deleted, substituted, inserted and/or added amino acids" is exemplified by from 1 to 20, 1 to 15, 1 to 10, 1 to 9, 1 to 8, 1 to 7, 1 to 6 (from 1 to several), 1 to 5, 1 to 4, 1 to 3, 1 or 2, or 1. A smaller number of deleted, substituted, inserted and/or added amino acids is generally more preferable. Any two or more types of changes from among the above deletions, substitutions, insertions and additions in amino acid residues may occur concurrently. Such proteins may be obtained by using a site-specific mutagenesis technique described in, for example, MOLECULAR CLONING, 3$^{RD}$ ED.; *Current Protocols in Molecular Biology; Nuc. Acids. Res.,* 10, 6487 (1982); *Proc. Natl. Acad. Sci. USA,* 79, 6409 (1982); *Gene* 34, 315 (1985); *Nuc. Acids. Res.,* 13, 4431 (1985); or *Proc. Natl. Acad. Sci. USA,* 82, 488 (1985).

Additional examples of the first region include (c) regions which have an amino acid sequence that is at least approximately 70%, at least approximately 75%, at least approximately 80%, at least approximately 85%, at least approximately 88%, at least approximately 90%, at least approximately 91%, at least approximately 92%, at least approximately 93%, at least approximately 94%, at least approximately 95%, at least approximately 96%, at least approximately 97%, at least approximately 98%, or at least approximately 99% identical with the amino acid sequence of SEQ ID NO: 1, and which have an activity or ability substantially similar to a region with the amino acid sequence of SEQ ID NO: 1. More specific examples of the first region include regions which have an amino acid sequence that is at least approximately 70%, at least approximately 75%, at least approximately 80%, at least approximately 85%, at least approximately 88%, at least approximately 90%, at least approximately 91%, at least approximately 92%, at least approximately 93%, at least approximately 94%, at least approximately 95%, at least approximately 96%, at least approximately 97%, at least approximately 98%, or at least approximately 99% identical with the amino acid sequence of SEQ ID NO: 1, and which have the activity or ability to bind to the Fc region of IgG. It is generally preferable for the numerical value indicating the above degree of identity to be higher. Identity between amino acid sequences or nucleotide sequences may be determined using a sequencing program such as BLAST (see, for example, Altzshul, S. F. et al., *J. Mol. Biol.,* 215, 403 (1990)) or FASTA (see, for example, Pearson, W. R., *Methods in Enzymology,* 183, 63 (1990)). When using BLAST or FASTA, the default parameters for the respective programs are employed.

Still further examples of the first region include (d) regions which have an amino acid sequence encoded by a polynucleotide that hybridizes under stringent conditions with a polynucleotide having a nucleotide sequence complementary to the nucleotide sequence set forth in SEQ ID NO: 2, and which have an activity or ability substantially similar to regions with the amino acid sequence set forth in SEQ ID NO: 1. Polynucleotides which hybridize under stringent conditions shall be described subsequently.

Second Region

As used herein, "second region" refers to regions having the amino acid sequence set forth in SEQ ID NO: 3 and regions having a substantially similar activity or ability as regions having the amino acid sequence set forth in SEQ ID NO: 3.

"Substantially similar activity or ability as regions having the amino acid sequence set forth in SEQ ID NO: 3" refers to, for example: (i) the ability of the foregoing region to bind to a peroxide of coelenterazine or a peroxide of a coelenterazine derivative; or (ii) the ability of the foregoing region to bind to a peroxide of coelenterazine or a peroxide of a coelenterazine derivative so as to form a holoprotein that emits light under the action of a calcium ion. Measurement of the light emission may be carried out by the methods described in, for example, Shimomura, O. et al., *Biochem. J*, 251, 405-410 (1988) and Shimomura, O. et al., *Biochem. J*, 261, 913-920 (1989). Specifically, the foregoing region is bound to coelenterazine or a coelenterazine derivative in the presence of oxygen, and the luminescence reaction can be initiated by adding a calcium solution. In addition, the luminescence activity or luminescence pattern can be measured using a luminometer. Luminometers that may be used include commercially available instruments, such as the AB-2200 (Atto Corporation) and the Centro LB 960 (Berthold Technologies).

Examples of the second region include (e) regions having the amino acid sequence set forth in SEQ ID NO: 3, and (f) regions which have an amino acid sequence with, in the amino acid sequence of SEQ ID NO: 3, one or more deleted, substituted, inserted and/or added amino acids, and which have an activity or ability that is substantially similar to that of a region having the amino acid sequence of SEQ ID NO: 3. Here, the range of "one or more" in the "amino acid sequence having one or more deleted, substituted, inserted and/or added amino acids" is exemplified by from 1 to 20, 1 to 15, 1 to 10, 1 to 9, 1 to 8, 1 to 7, 1 to 6 (from 1 to several), 1 to 5, 1 to 4, 1 to 3, 1 or 2, or 1. A smaller number of deleted, substituted, inserted and/or added amino acids is generally more preferable.

Additional examples of the second region include (g) regions which have an amino acid sequence that is at least approximately 70%, at least approximately 75%, at least approximately 80%, at least approximately 85%, at least approximately 88%, at least approximately 90%, at least approximately 91%, at least approximately 92%, at least approximately 93%, at least approximately 94%, at least approximately 95%, at least approximately 96%, at least approximately 97%, at least approximately 98%, or at least approximately 99% identical with the amino acid sequence of SEQ ID NO: 3, and which have an activity or ability substantially similar to a region with the amino acid sequence of SEQ ID NO: 3. More specific examples of the second region include regions which have an amino acid sequence that is at least approximately 70%, at least approximately 75%, at least approximately 80%, at least approximately 85%, at least approximately 88%, at least approximately 90%, at least approximately 91%, at least approximately 92%, at least approximately 93%, at least approximately 94%, at least approximately 95%, at least approximately 96%, at least approximately 97%, at least approximately 98%, or at least approximately 99% identical with the amino acid sequence of SEQ ID NO: 3; and which have (i) the ability to bind to a peroxide of coelenterazine or a peroxide of a coelenterazine derivative or (ii) the ability to bind to a peroxide of coelenterazine or a peroxide of a coelenterazine derivative and form a holoprotein which emits light under the action of a calcium ion. It is generally preferable for the numerical value indicating the above degree of identity to be higher.

Still further examples of the second region include (h) regions which have an amino acid sequence encoded by a polynucleotide that hybridizes under stringent conditions with a polynucleotide having a nucleotide sequence complementary to the nucleotide sequence set forth in SEQ ID NO: 4, and which have an activity or ability substantially similar to regions with the amino acid sequence set forth in SEQ ID NO: 3. Polynucleotides which hybridize under stringent conditions shall be described subsequently.

2. Polynucleotide of the Invention

The invention also provides a polynucleotide encoding the above-described fusion protein of the invention. The polynucleotide of the invention may be any polynucleotide having a nucleotide sequence that encodes the fusion protein of the invention, although DNA is preferred. Exemplary DNA includes genomic DNA, genomic DNA libraries, cellular or tissue cDNA, cellular or tissue cDNA libraries, and synthetic DNA. The vectors used in the libraries are not subject to any particular limitation, and may be, for example, bacteriophages, plasmids, cosmids or phagemids. Also, amplification may be carried out directly by a reverse transcription polymerase chain reaction (abbreviated below as "RT-PCR") using total RNA or a mRNA fraction prepared from the above-mentioned cell or tissue.

The polynucleotide of the invention is exemplified by polynucleotides which include:

(1) a first coding sequence selected from the group of:

(a) a polynucleotide comprising a polynucleotide having the nucleotide sequence set forth in SEQ ID NO: 2, (b) a polynucleotide including a polynucleotide which hybridizes under stringent conditions to a polynucleotide having a nucleotide sequence complementary to the nucleotide sequence of SEQ ID NO: 2, and which encodes a region having the ability to bind to the Fc region of IgG, (c) a polynucleotide including a polynucleotide encoding a region having the amino acid sequence as set forth in SEQ ID NO: 1, and (d) a polynucleotide including a polynucleotide encoding a region which has an amino acid sequence with, in the amino acid sequence of SEQ ID NO: 1, one or more deleted, substituted, inserted and/or added amino acids, and which has the ability to bind to the Fc region of IgG; and (2) a second coding sequence selected from the group of:

(e) a polynucleotide including a polynucleotide having the nucleotide sequence set forth in SEQ ID NO: 4, (f) a polynucleotide including a polynucleotide which hybridizes under stringent conditions to a polynucleotide having a nucleotide sequence complementary to the nucleotide sequence of SEQ ID NO: 4, and which encodes a region having the ability to bind to a peroxide of coelenterazine or a peroxide of a coelenterazine derivative so as to form a holoprotein that emits light under the action of a calcium ion, (g) a polynucleotide including a polynucleotide encoding a region having the amino acid sequence as set forth in SEQ ID NO: 3, and (h) a polynucleotide including a polynucleotide encoding a region which has an amino acid sequence with, in the amino acid sequence of SEQ ID NO: 3, one or more deleted, substituted, inserted and/or added amino acids, and which encodes a region having the ability to bind to a peroxide of coelenterazine or a peroxide of a coelenterazine derivative so as to form a holoprotein that emits light under the action of a calcium ion.

"Polynucleotides (e.g., DNA) which hybridize under stringent conditions" refers herein to polynucleotides (e.g., DNA) which are obtained by, for example, colony hybridization, plaque hybridization or Southern hybridization using as the probe all or part of a polynucleotide having a nucleotide sequence complementary to the nucleotide sequence of SEQ ID NO: 2 or 4 or a polynucleotide encoding the amino acid sequence of SEQ ID NO: 1 or 3. Specific examples include polynucleotides which can be identified by carrying out hybridization at 65° C. and in the presence of 0.7 to 1.0 mol/L NaCl using a filter on which polynucleotide from a colony or plaque has been immobilized, then washing the filter at 65° C. with an SSC (saline-sodium citrate) solution having a concentration in a range of 0.1× to 2× (a 1× SSC solution being composed of 150 mmol/L of sodium chloride and 15 mmol/L of sodium citrate).

Hybridization may be carried out in general accordance with methods described in, for example, Sambrook, J. et al., MOLECULAR CLONING: A LABORATORY MANUAL, Third Edition (Cold Spring Harbor Laboratory Press, 2001) (abbreviated as "MOLECULAR CLONING, 3$^{RD}$ ED."); Ausbel, F. M. et al., CURRENT PROTOCOLS IN MOLECULAR BIOLOGY, Supplements 1 to 38 (John Wiley & Sons, 1987-1997); and Glover, D. M. and Hames, B. D., DNA CLONING 1: CORE TECHNIQUES, A PRACTICAL APPROACH, Second Edition (Oxford University Press, 1995).

In the specification, "stringent conditions" may refer to low stringency conditions, moderate stringency conditions or high stringency conditions. "Low stringency conditions" are, for example, 5× SSC, 5× Denhart's solution, 0.5% (w/v) SDS and 50% (v/v) formamide at 32° C. "Moderate stringency conditions" are, for example, 5× SSC, 5× Denhart's solution, 0.5% (w/v) SDS and 50% (v/v) formamide at 42° C. "High stringency conditions" are, for example, 5× SSC, 5× Denhart's solution, 0.5% (w/v) SDS and 50% (v/v) formamide at 50° C. The more stringent the conditions, the higher the complementarity required for double strand formation. Under these conditions, a polynucleotide (e.g., DNA) of higher homology is expected to be obtained efficiently at higher temperature, although multiple factors are involved in hybridization stringency, including temperature, probe concentration, probe length, ionic strength, time and salt concentration, and one skilled in the art may appropriately select these factors to achieve a similar stringency.

An example of a commercial kit that may be used for hybridization is AlkPhos Direct Labeling Reagents (Amersham Pharmacia Biotech). According to the protocol that comes with the kit, following overnight incubation with a labeled probe, the membrane is washed with a primary wash buffer containing 0.1% (w/v) SDS at 55° C., after which the hybridized DNA can be detected.

Other hybridizable polynucleotides include, when calculations are done with a sequencing program such as FASTA or BLAST using the default parameters, DNA that is at least approximately 60%, at least approximately 65%, at least approximately 70%, at least approximately 75%, at least approximately 80%, at least approximately 85%, at least approximately 88%, at least approximately 90%, at least approximately 92%, at least approximately 95%, at least approximately 97%, at least approximately 98%, at least approximately 99%, at least approximately 99.3%, at least approximately 99.5%, at least approximately 99.7%, at least approximately 99.8%, or at least approximately 99.9% identical to polynucleotides encoding the amino acid sequence of SEQ ID NO: 1 or 3. The identity of an amino acid sequence or a nucleotide sequence can be determined using the above-described method.

A polynucleotide encoding a region having, with respect to a given amino acid sequence, one or more deleted, substituted, inserted and/or added amino acids, may be obtained using a site-specific mutagenesis technique (see, for example, Gotoh, T. et al., *Gene,* 152, 271-275 (1995); Zoller, M. J. and Smith, M., *Methods Enzymol.,* 100, 468-500 (1983); Kramer, W. et al., *Nucleic Acids Res.,* 12, 9441-9456 (1984); Kramer, W. and Fritz, H. J., *Methods Enzymol.,* 154, 350-367 (1987); Kunkel, T. A., *Proc. Natl. Acad. Sci. USA,* 82, 488-492 (1985); Kunkel, *Methods Enzymol.,* 5, 2763-2766 (1988)), and methods employing amber mutation (see, for example, the gapped duplex method in *Nucleic Acids Res.,* 12, 9441-9456 (1984)).

Alternatively, a mutation may be introduced onto the polynucleotide via, for example, a polymerase chain reaction (PCR) using a set of primers bearing on the respective 5' ends a sequence in which the target mutation (deletion, addition, substitution and/or insertion) has been introduced (see, for example, Ho, S, N. et al., *Gene,* 77, 51 (1989)).

Also, a polynucleotide encoding a protein partial fragment, which is one type of deletion variant, may be obtained by using as the primers an oligonucleotide having a sequence which matches the nucleotide sequence at the 5' end of the region of the protein-encoding polynucleotide that codes for the partial fragment to be produced and an oligonucleotide having a sequence complementary to the nucleotide sequence at the 3' end thereof, and carrying out a PCR in which the polynucleotide encoding the protein serves as the template.

Illustrative examples of the polynucleotide of the invention include polynucleotides including polynucleotides encoding the fusion protein having the amino acid sequence of SEQ ID NO: 5. Examples of polynucleotides including polynucleotides encoding the fusion protein having the amino acid sequence of SEQ ID NO: 5 include polynucleotides including polynucleotides having the nucleotide sequence of SEQ ID NO: 6.

The polynucleotide of the invention may include a polynucleotide encoding an amino acid sequence for enhancing translation and/or a polynucleotide encoding a peptide sequence for purification. A polynucleotide which includes a nucleotide sequence encoding an amino acid sequence for enhancing translation and is used in the technical field of the invention may be employed as the polynucleotide encoding an amino acid sequence for enhancing translation. Examples of amino acid sequences for enhancing translation include those mentioned above. A polynucleotide which includes a nucleotide sequence encoding a peptide sequence for purification and is used in the technical field of the invention may be employed as the polynucleotide encoding a peptide sequence for purification. Examples of peptide sequences for purification include those mentioned above.

3. Recombinant Vectors and Transformants of the Invention

The invention further provides a recombinant vector and a transformant which include the above-described polynucleotide of the invention.

(1) Construction of Recombinant Vector

The recombinant vector of the invention may be obtained by ligating (inserting) the polynucleotide (DNA) of the invention to a suitable vector. More specifically, the recombinant vector may be obtained by cleaving purified polynucleotide (DNA) with a suitable restriction enzyme, then inserting the cleaved polynucleotide to a restriction enzyme site or multicloning site on a suitable vector, and ligating the polynucleotide to the vector. The vector for inserting the inventive polynucleotide is not subject to any particular limitation, provided it is capable of replication in the host. Vectors that may be used for this purpose include plasmids, bacteriophages, and animal viruses. Illustrative examples of suitable plasmids include plasmids from *E. coli* (e.g., pBR322, pBR325, pUC118 and pUC119), plasmids from *Bacillus subtilis* (e.g., pUB110 and pTP5), and plasmids from yeasts (e.g., YEp13, YEp24 and YCp50). An example of a suitable bacteriophage is the λ phage. Examples of suitable animal viruses include retroviruses, vaccinia viruses and insect viruses (e.g., baculoviruses).

Alternatively, in the invention, preferred use may be made of, for example, pCold I vector, pCold II vector, pCold III vector, or pCold IV vector (all products of Takara Bio Inc.). As shown specifically in the subsequent examples, when expression is induced using these vectors in a prokaryotic cell as the host, production of the inventive fusion protein as a soluble protein can be made to occur within the cytoplasm of the host cell.

The polynucleotide of the invention is generally ligated downstream from the promoter in a suitable vector in such a way as to be expressible. For example, if the host during transformation is an animal cell, preferred promoters include promoters from SV40, retrovirus promoters, metallothionein promoters, heat shock promoters, cytomegalovirus promoters and the SRα promoter. If the host is a genus *Escherichia* organism, preferred promoters include the Trp promoter, the T7 promoter, the lac promoter, the recA promoter, the λPL promoter and the lpp promoter. If the host is a genus *Bacillus* organism, preferred promoters include the SPO1 promoter, the SPO2 promoter and the penP promoter. If the host is a yeast, preferred promoters include the PHO5 promoter, the PGK promoter, the GAP promoter, the ADH1 promoter and the GAL promoter. If the host is an insect cell, preferred promoters include the polyhedrin promoter and the P10 promoter.

In addition to the above, the recombinant vector used in the invention may contain, if desired, an enhancer, a splicing signal, a poly(A) addition signal, a ribosome binding sequence (SD sequence), a selective marker and the like. Illustrative examples of selective markers include the dihydrofolate reductase gene, the ampicillin resistance gene and the neomycin resistance gene.

The recombinant vector of the invention may additionally include a polynucleotide having a nucleotide sequence encoding an amino acid sequence for enhancing translation and/or a polynucleotide having a nucleotide sequence encoding a peptide sequence for purification. A polynucleotide which includes a nucleotide sequence encoding an amino acid sequence for enhancing translation and is used in the technical field of the invention may be employed as the polynucleotide encoding an amino acid sequence for enhancing translation. Examples of amino acid sequences for enhancing translation include those mentioned above. A polynucleotide which includes a nucleotide sequence encoding a peptide sequence for purification and is used in the technical field of the invention may be employed as the polynucleotide encoding a peptide sequence for purification. Examples of peptide sequences for purification include those mentioned above.

(2) Preparation of Transformant

The transformant can be created by introducing into a suitable host the recombinant vector, obtained as described above, which includes the polynucleotide of the invention (i.e., a polynucleotide encoding the fusion protein of the invention). The host is not subject to any particular limitation, provided it is capable of expressing the polynucleotide (DNA) of the invention. Examples include bacteria of the genera *Escherichia, Bacillus, Pseudomonas* and *Rhizobium*, yeasts, animal cells and insect cells. Bacteria of the genus *Escherichia* include *E. coli*. Bacteria of the genus *Bacillus* include *B. subtilis*. Bacteria of the genus *Pseudomonas* include *P. putida*. Bacteria of the genus *Rhizobium* include *R. meliloti*. Yeasts include *Saccharomyces cerevisia* and *Schizosaccharomyces pombe*. Animal cells include COS cells and CHO cells. Insect cells include Sf9 and Sf21.

Introduction of the recombinant vector into the host and transformation thereby may be carried out by any of various commonly used methods. Examples of suitable methods for introducing the recombinant vector into the host cell include the calcium phosphate method (*Virology*, 52, 456-457 (1973)), lipofection (*Proc. Natl. Acad. Sci. USA*, 84, 7413 (1987)), and electroporation (*EMBO J.*, 1, 841-845 (1982)). Examples of methods for transforming genus *Escherichia* bacteria include the methods described in *Proc. Natl. Acad. Sci. USA*, 69, 2110 (1972), and *Gene*, 17, 107 (1982). Methods for transforming genus *Bacillus* bacteria include the methods described in *Molecular & General Genetics*, 168, 111 (1979). Methods for transforming yeasts include the methods described in *Proc. Natl. Acad. Sci. USA*, 75, 1929 (1978). Methods for transforming animal cells include the methods described in *Virology*, 52, 456 (1973). Methods for transforming insect cells include the methods described in *Bio/Technology*, 6, 47-55 (1988). A transformant created by transformation with a recombinant vector containing the polynucleotide which codes for the fusion protein of the invention (i.e., the polynucleotide of the invention) may be obtained in this way.

4. Production of Inventive Fusion Protein

The invention also provides a method for producing the inventive fusion protein, which method includes the step of culturing the above-described transformant so as to induce the transformant to produce the fusion protein of the invention. The inventive fusion protein may be produced by culturing the transformant under conditions that allow the polynucleotide (DNA) encoding the fusion protein to be expressed, thereby inducing formation and accumulation of the inventive fusion protein, then isolating and purifying the fusion protein.

Culturing the Transformant:

The transformant of the invention may be cultivated by a conventional method used for culturing hosts. In such cultivation, the fusion protein of the invention is formed by the transformant and accumulates within the transformant or the culture broth.

The medium for culturing the transformant using a genus *Escherichia* or *Bacillus* bacterium as the host may be a natural medium or a synthetic medium, provided it is a medium which includes the carbon sources, nitrogen sources, inorganic salts and other nutrients essential for growth of the transformant, and in which the transformant can be efficiently grown. Examples of carbon sources that may be used include carbohydrates such as glucose, fructose, sucrose and starch; organic acids such as acetic acid and propionic acid; and alcohols such as ethanol and propanol. Examples of nitrogen sources that may be used include ammonia, ammonium salts of inorganic or organic acids, such as ammonium chloride, ammonium sulfate, ammonium acetate and ammonium phosphate, other nitrogen-containing compounds, and also peptone, meat extract and corn steep liquor. Examples of inorganic salts include monobasic potassium phosphate, dibasic potassium phosphate, magnesium phosphate, magnesium sulfate, sodium chloride, ferrous sulfate, manganese sulfate, copper sulfate and calcium carbonate. If necessary, antibiotics such as ampicillin or tetracycline may be added to the medium during culturing. If the transformant to be cultured has been obtained by transformation with an expression vector using an inducible promoter as the promoter, where necessary, an inducer may also be added to the medium. For example, isopropyl-β-D-thiogalactopyranoside (IPTG) may be added to the medium when culturing a transformant obtained by transformation with an expression vector using a Lac promoter, and indoleacrylic acid (IAA) may be added to the medium when culturing a transformant obtained by transformation with an expression vector using a trp promoter.

When the host is a bacterium of the genus *Escherichia*, incubation is generally carried out at approximately 15 to 43° C. for approximately 3 to 24 hours. If necessary, aeration and stirring may be applied. When the host is a bacterium of the genus *Bacillus*, incubation is generally carried out at approximately 30 to 40° C. for approximately 6 to 24 hours. If necessary, aeration and stirring may be applied.

Media for culturing the transformant when the host is a yeast are exemplified by Burkholder's minimal medium (*Proc. Natl. Acad. Sci. USA,* 77, 4505 (1980)) and an SD medium containing 0.5% (w/v) casamino acids (*Proc. Natl. Acad. Sci. USA,* 81, 5330 (1984)). The pH of the medium is preferably adjusted to approximately 5 to 8. Culturing is generally carried out at approximately 20 to 35° C. for approximately 24 to 72 hours. If necessary, aeration and stirring may be applied.

Media for culturing the transformant when the host is an animal cell are exemplified by MEM media containing approximately 5 to 20% (v/v) fetal calf serum (*Science,* 122, 501 (1952)) and DMEM media (Virology, 8, 396 (1959)). The pH of the medium is preferably adjusted to approximately 6 to 8. Culturing is generally carried out at approximately 30 to 40° C. for approximately 15 to 60 hours. If necessary, aeration and stirring may be applied.

Media for culturing the transformant when the host is an insect cell are exemplified by Grace's insect medium (*Nature,* 195, 788 (1962)) to which additives such as 10% (v/v) immobilized bovine serum have been suitably added. The pH of the medium is preferably adjusted to approximately 6.2 to 6.4. Culturing is generally carried out at approximately 27° C. for approximately 3 to 5 hours. If necessary, aeration and stirring may be applied.

Isolation and Purification of Inventive Fusion Protein:

The fusion protein of the invention may be obtained by isolating and purifying the inventive fusion protein from the above-described culture. As used herein, "culture" refers to any one of the following: a culture broth, cultured bacteria, cultured cells, and the products obtained by disrupting cultured bacteria or cultured cells. Conventional methods may be used to isolate and purify the fusion protein of the invention.

Specifically, when the fusion protein of the invention accumulates within cultured bacteria or within cultured cells, following the completion of cultivation, an extract of the fusion protein of the invention may be obtained by a conventional method such as centrifugation or filtration after using a conventional technique (e.g., ultrasound, lysozymes, freezing and thawing) to disrupt the bacteria or cells. When the inventive fusion protein accumulates in the periplasmic space, following the completion of cultivation, an extract containing the target protein may be obtained by a conventional method such as osmotic shock. When the fusion protein of the invention accumulates in the culture broth, following the completion of cultivation, a culture supernatant containing the inventive fusion protein may be obtained by using a conventional method such as centrifugation or filtration to separate the culture supernatant from the bacteria or cells.

Purification of the inventive fusion protein present in the extract or culture supernatant obtained as described above may be carried out by a conventional method of separation and purification. Examples of separation and purification methods that may be used include ammonium sulfate precipitation, gel filtration chromatography, ion-exchange chromatography, affinity chromatography, reversed-phase high-performance liquid chromatography, dialysis, and ultrafiltration, as well as suitable combinations thereof. If the inventive fusion protein includes the above-described peptide sequence for purification, it is preferable to carry out purification using the same. Specifically, if the fusion protein of the invention contains a histidine tag sequence, use may be made of nickel chelate affinity chromatography; if the fusion protein of the invention includes the glutathione-binding domain of S-transferase, use may be made of affinity chromatography using a glutathione-binding gel; if the fusion protein of the invention includes the amino acid sequence of Protein A, use may be made of antibody affinity chromatography.

The holoprotein (photoprotein) of the invention which emits light in a degree that depends on the calcium ion concentration may be prepared by incubating at a low temperature the purified apoprotein of the invention together with the light-emitting substrate coelenterazine or a derivative thereof in the presence of a reducing agent (e.g., mercaptoethanol, dithiothreitol) and oxygen.

5. Uses of the Inventive Fusion Protein

Detection and Assay of Calcium Ions

As noted above, the inventive fusion protein (apoprotein) is capable of bonding with a peroxide of coelenterazine or a peroxide of a coelenterazine derivative to form a holoprotein (photoprotein) which can emit light under the action of calcium ions. Moreover, the holoprotein of the invention exists as a complex (photoprotein of the invention) which can emit light under the action of calcium ions in the presence of oxygen. Accordingly, the fusion protein of the invention and the holoprotein of the invention may be used for detecting and assaying calcium ions. The detection or assay of calcium ions may be carried out by using a luminometer to measure the light emitted by the photoprotein of the invention owing to the action of calcium ions. Luminometers that may be used include commercially available instruments, such as the Centro LB 960 (Berthold Technologies). Quantitative determination of the calcium ion concentration may be carried out by first preparing a luminescence standard curve for known calcium ion concentrations using the holoprotein.

Use as Marker for Detection by Luminescence

As noted above, the fusion protein of the invention is capable of forming a holoprotein (photoprotein) that can emit light through the action of calcium ions. Moreover, because it has the ability to bind to IgG, it can be used, for example, to detect IgG in immunoassays. Such detection of IgG may be carried out by a conventional method. Specifically, IgG may be detected by having the fusion protein of the invention bond with the IgG, then emit light under the action of calcium ions. Alternatively, the fusion protein of the invention may be bonded with IgG, after which the fusion protein of the invention may be brought into contact with coelenterazine or a coelenterazine derivative in the presence of oxygen so as to form the photoprotein of the invention, which may then be induced to emit light under the action of calcium ions.

6. Kits According to the Invention

The invention also provides kits which include any of the following: fusion proteins of the invention, holoproteins of the invention, polynucleotides of the invention, recombinant vectors of the invention, and transformants of the invention. The inventive kits may additionally include coelenterazine or a derivative thereof, and may be manufactured with conventionally used materials and methods. The inventive kits may also include sample tubes, plates, instructions for the user, solutions, buffers, reagents, and either samples suitable for standardization or control samples.

The inventive kits may be employed for the above-described detection or assay of calcium ions, or for the detection or assay of IgG.

Where no particular explanation is given in the preferred embodiments for working the invention or the examples of the invention, use will typically be made of the methods described in standard collections of protocols, such as J. Sambrook, E. F. Fritsch & T. Maniatis (Eds.), MOLECULAR CLONING, A LABORATORY MANUAL ($3^{RD}$ EDITION) (Cold Spring Harbor, N.Y.: Cold Spring Harbor Press, 2001) and F. M. Ausubel, R. Brent, R. E. Kingston, D. D. Moore, J. G. Seidman, J. A. Smith, K. Struhl (Eds.), CURRENT PROTOCOLS IN MOLECULAR BIOLOGY (John Wiley & Sons, Ltd.), or modifications or variations thereof. When commercially available reagent kits and measurement equipment are used, unless noted otherwise herein, the protocols provided therewith will typically be followed.

The objects, features, advantages and ideas of the invention will be apparent to those skilled in the art from the description provided in the specification, and the invention will be readily practicable by those skilled in the art on the basis of the description appearing herein. The Description of the Preferred Embodiments and the Examples which show preferred modes for practicing the invention are included for the purpose of illustration and explanation, and are not intended to limit the scope of the claims. It will be apparent to those skilled in the art that various modifications may be made in how the invention is practiced based on described aspects in the specification without departing from the spirit and scope of the invention disclosed herein.

Sequence numbers in the Sequence Listing of the present specification indicate the following sequences.

SEQ ID NO: 1 shows the amino acid sequence of the ZZ domain;

SEQ ID NO: 2 shows the nucleotide sequence of DNA which codes for the amino acid sequence set forth in SEQ ID NO: 1;

SEQ ID NO: 3 shows the amino acid sequence of apoaequorin;

SEQ ID NO: 4 shows the nucleotide sequence of DNA which codes for the amino acid sequence set forth in SEQ ID NO: 3;

SEQ ID NO: 5 shows the amino acid sequence of the ZZ-apoaequorin fusion protein encoded by the DNA which codes for the ZZ-apoaequorin fusion protein and which has been inserted into the expression vector pCold-ZZ-AQ constructed in Example 1;

SEQ ID NO: 6 shows the nucleotide sequence of DNA which codes for the ZZ-apoaequorin fusion protein and which has been inserted into the expression vector pCold-ZZ-AQ constructed in Example 1;

SEQ ID NO: 7 shows the nucleotide sequence of a primer used in Example 1;

SEQ ID NO: 8 shows the nucleotide sequence of a primer used in Example 1;

SEQ ID NO: 9 shows the nucleotide sequence of a primer used in Example 1; and SEQ ID NO: 10 shows the nucleotide sequence of a primer used in Example 1.

EXAMPLES

Examples are given below to more fully illustrate the invention, and should not be construed as limiting the invention.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted, to limit the scope of the invention.

Reference Example 1

A Protein A-apoaequorin fusion protein was prepared by the method described below. First, the Protein A-apoaequorin (the latter component sometimes being abbreviated below as "apoAQ") fusion protein was expressed using the expression vector and method of expression described in Japanese Patent Application Laid-open No. H2-154688 (Japanese Patent Application No. S63-308424) previously filed by the inventors. The Protein A-apoAQ fusion protein was purified by the method described in a published article by the inventors (*Biochem. Biophys. Res. Commun.*, 171, 169-174 (1990)). Specifically, the Protein A-apoAQ fusion protein expression vector pAAQ-1 expresses a fusion protein composed of a 36-residue secretory signal for Protein A, a 271-residue region which includes the IgG-binding domain of protein A, and apoaequorin (188 residues). The amount of the Protein A-apoAQ fusion protein expressed in *E. coli*, as calculated from the luminescence activity, was approximately 8 mg in 200 mL of cultured cells. The purified Protein A-apoAQ fusion protein obtained from a crude extract of these cells by a combination of IgG Sepharose column chromatography, Sepharose 12 Gel chromatography and reverse-phase chromatography, was a heteroprotein having molecular weights of 42 KDa and 43 KDa. The purified Protein A-apoAQ fusion protein had a purity of at least 95% and was obtained in a yield of approximately 30 μg. Using a method like that described in Example 3 below, Protein A-AQ was regenerated from Protein A-apoAQ by incubation for one full day at 4° C. together with the light-emitting substrate coelenterazine in the presence of a reducing agent. The regeneration yield was at least 95%.

Example 1

Construction of ZZ-ApoAQ Fusion Protein Expression Vector

The ZZ gene and the aequorin gene were prepared by the methods described below in order to express the recombinant ZZ-apoAQ fusion protein in *E. coli*. The ZZ gene encoding the ZZ domain which is the IgG-binding domain was prepared by the polymerase chain reaction (PCR) method from pEZZ18 (Amersham Bioscience). The aequorin gene which codes for apoaequorin was prepared by the PCR method from pAM-HE containing a HindIII-EcrRI fragment that is the region coding for pAQ440 (Japanese Patent Application Laid-open No. S61-135586). The pCold II vector (Takara Bio) was used as the expression vector. The following method was used to construct the ZZ-apoAQ fusion protein expression vector.

First, a polymerase chain reaction (PCR) (cycle conditions: 25 cycles, each consisting of 1 minute at 94° C., 1 minute at 50° C. and 1 minute at 72° C.) was carried out by use of a PCR kit (Takara Bio) with pAM-HE as the template and using the following two PCR primers: AQ-EcoRI-Met (5' CCG-GAATTC-ATG-AAA-CTT-ACA-TCA-GAC-TTC-GAC-AAC 3' (SEQ ID NO: 7); the EcoRI restriction enzyme site is underlined) and AQ-C-SalI (5' CGCGTCGAC-TTA-GGG-GAC-AGC-TCC-ACC-GTA-GAG-CTT 3' (SEQ ID NO: 8); the SalI restriction enzyme site is underlined), thereby amplifying the desired aequorin gene region. The resulting DNA fragment was purified with a PCR purification kit (Qiagen). The purified DNA fragment was then digested with the restriction enzymes EcoRI/SalI by a conventional method, following which it was ligated to the restriction enzyme EcoRI/SalI site on the pCold II vector, thereby constructing the expression vector pCold-AQ.

In a separate procedure, a PCR (cycle conditions: 25 cycles, each consisting of 1 minute at 94° C., 1 minute at 50° C. and 1 minute at 72° C.) was carried out by use of a PCR kit (Takara Bio) with pEZZ18 as the template and using the following two PCR primers: 6ZZ-N-NdeI (5' CCG CAT ATG GCG CAA CAC GAT GAA GCC GTG 3' (SEQ ID NO: 9); the NdeI restriction enzyme site is underlined) and 7ZZ-C-BamHI (5' GGC GGA TCC CGA GCT CGA ATT TGC GTC TAC 3' (SEQ ID NO: 10); the BamHI restriction enzyme site is underlined), thereby amplifying the desired DNA region. The resulting DNA fragment was purified with a PCR purification kit (Qiagen). The purified DNA fragment was then digested with the restriction enzymes NdeI/BamHI by a conventional method, following which it was ligated to the restriction enzyme NdeI/BamHI site on the pCold-AQ vector, thereby constructing the expression vector pCold-ZZ-AQ shown in FIG. 1. This expression vector was inducible at a low temperature, and the expressed ZZ-apoAQ had a histidine tag at the amino-terminal end.

Example 2

Preparation of Recombinant ZZ-ApoAQ Fusion Protein

Preparation of the Recombinant ZZ-apoAQ Fusion Protein was Carried Out, as described below, by expressing the recombinant ZZ-apoAQ fusion protein in E. coli, then extracting the expressed fusion protein and purifying the expressed fusion protein using various chromatographic methods.

Measurement of the luminescent activity by the fusion protein after purification was carried out as follows. First, the crude ZZ-apoAQ fusion protein solution, 2-mercaptoethanol (1 μl) and the substrate coelenterazine dissolved in ethanol (1 μg/μl) were mixed in 1 mL of a 50 mM Tris-HCl (pH 7.6) buffer, following which the mixture was left to stand on ice (4° C.) for 2 hours, thereby preparing a ZZ-AQ fusion protein having a luminescent activity. The luminescence reaction was initiated by adding 100 μl of 50 mM $CaCl_2$ to the resulting ZZ-AQ fusion protein solution, and the luminescent activity was measured for a period of 10 seconds using a PSN AB2200 luminometer (Atto Corporation). The luminescent activity (e.g., maximum value (Imax)) was rated in terms of the relative luminescence intensity expressed in relative light units (rlu).

(1) Expression of Recombinant ZZ-ApoAQ Fusion Protein in E. coli

The expression vector pCold-ZZ-AQ obtained in Example 1 was inserted into the E. coli strain BL21 by the polyethylene glycol method, thereby obtaining a transformant. The transformant was then cultured for 18 hours at 37° C., following which it was inoculated onto 10 mL of LB liquid medium (composed of 10 g of bactotryptone, 5 g of yeast extract and 5 g of sodium chloride per liter of water; pH 7.2) containing ampicillin (100 μg/mL) and additionally cultured at 37° C. for 18 hours. The culture was then added to 2 liters of fresh LB liquid medium (400 mL×5) and cultured at 37° C. for 4.5 hours. After culturing, the liquid culture was cooled over ice water, then isopropyl-β-D(−)-thiogalactopyranoside (IPTG; produced by Wako Pure Chemical Industries) was added to the culture to a final concentration of 0.1 mM and culturing was carried out for 17 hours at 15° C. The cultured cells were then harvested by centrifugation (5 minutes at 5,000 rpm (6,000×g)) using a cooling centrifuge.

(2) Extraction of ZZ-ApoAQ Fusion Protein from Cultured Bacteria

After being harvested in (1) above, the cultured bacteria were suspended in 200 mL (40 mL×5) of 50 mM Tris-HCl (pH 7.6), and subjected three times to 2 minutes each of ultrasonic disruption under ice cooling (Branson model 250 Sonifier). The resulting cell ultrasonicate was then centrifugally separated at 10,000 rpm (12,000×g) for 20 minutes. The soluble fraction thus obtained used as the starting material for ZZ-apoAQ fusion protein purification.

(3) Purification of ZZ-ApoAQ Fusion Protein by Q-Sepharose Column Chromatography The soluble fraction (200 mL) obtained in (2) above was applied to a Q-Sepharose column (Amersham Bioscience; column size: 2.5 cm (dia)×6 cm) equilibrated with 50 mM Tris-HCl (pH 7.6) and adsorbed, following which the column was washed with 250 mL of 50 mM Tris-HCl (pH 7.6). The protein adsorbed by the column was subjected to linear gradient elution with a total of 100 mL of sodium chloride solutions having sodium chloride concentrations ranging from 0 to 1.0 M. ZZ-apoAQ fusion protein having a luminescent activity was confirmed to be eluted at sodium chloride concentrations of 0.45 to 0.65 M (25 mL; ZZ-apoAQ active fraction).

(4) Purification of ZZ-ApoAQ Fusion Protein by Nickel Chelate Column Chromatography The ZZ-apoAQ active fraction eluted from the Q-Sepharose column was applied to a nickel chelate column (Amersham Bioscience; column size: 1.5 cm (dia)×5 cm) equilibrated with 50 mM Tris-HCl (pH 7.6), and the ZZ-apoAQ fusion protein was adsorbed. The adsorbed ZZ-apoAQ fusion protein was subjected to linear gradient elution with a total of 100 mL of imidazole solutions having imidazole concentrations ranging from 0 to 0.3 M (Wako Pure Chemical Industries). ZZ-apoAQ fusion protein having a luminescent activity was confirmed to be eluted at imidazole concentrations of from 0.06 to 0.12 M (26 mL; ZZ-apoAQ active fraction).

(5) Purification of ZZ-ApoAQ Fusion Protein by IgG-Sepharose Column Chromatography Part of the ZZ-apoAQ active fraction eluted from the nickel chelate column was concentrated using an Amicon Ultra-4 Centrifugal Filter Device (molecule weight cutoff, 10,000; manufactured by Millipore Corporation). Next, 4 mL of the concentrated solution was applied to and IgG-Sepharose 6 Fast Flow column (Amersham Bioscience; column size: 1.5 (dia)×4 cm), and the ZZ-apoAQ fusion protein was adsorbed. The ZZ-apoAQ fusion protein adsorbed by the column was eluted with 0.5 M ammonium acetate (pH 3.4) (Wako Pure Chemical Industries).

Figure 2:
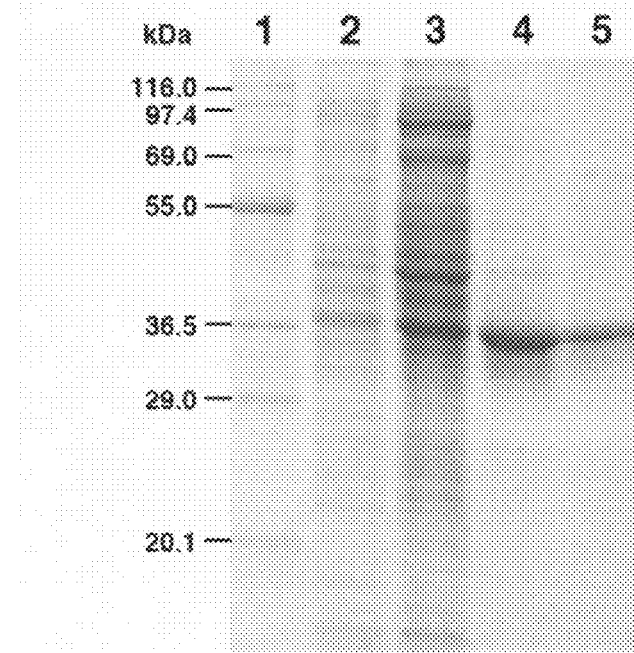
FIG. 2 shows the results of SDS-PAGE analysis at the stage of ZZ-apoaequorin purification. SDS-PAGE analysis was carried out with a 12% separation gel at 94° C. The specimens in the respective lanes were as follows. Lane 1: Protein molecular weight markers (Tefco): β-galactosidase (116,000), phospholipase B (97,400), bovine serum albumin (69,000), glutamate dehydrogenase (55,000), lactate dehydrogenase (36,500), carbonate dehydrogenase (29,000), trypsin inhibitor (20,100); Lane 2: Supernatant (protein, 5.4 μg) obtained by the centrifugation at 12,000 g of an ultrasonicate of a transformed strain of *E. coli* which expressed recombinant ZZ-apoAQ; Lane 3: Fraction eluted from Q-Sepharose column (protein, 16 μg); Lane 4: Fraction eluted from nickel chelate column (protein, 4.8 μg); Lane 5: Fraction eluted from IgG Sepharose column (protein, 1.3 μg)

As shown in FIG. 2, the purity was confirmed to be at least 95% by 12% SDS-polyacrylamide electrophoresis.

The purification yields are shown in Table 1. The amount of purified ZZ-apoAQ having a purity of at least 95% obtained by IgG-Sepharose column chromatography was 7.8 mg.

TABLE 1

| Purification Step | Total Amount (mL) | Protein Conc. (mg/mL) | Total Protein (mg) | Activity ($\times 10^{11}$ rlu/mL) | Relative Activity ($\times 10^{10}$ rlu/mg) | Total Activity ($\times 10^{12}$ rlu) | Yield (%) | Purification Coefficient |
|---|---|---|---|---|---|---|---|---|
| Supernatant (12,000 × g) of Ultrasonicate | 200 | 2.7 | 540 | 0.36 | 1.33 | 7.20 | 100 | 1.00 |

TABLE 1-continued

| Purification Step | Total Amount (mL) | Protein Conc. (mg/mL) | Total Protein (mg) | Activity ($\times 10^{11}$ rlu/mL) | Relative Activity ($\times 10^{10}$ rlu/mg) | Total Activity ($\times 10^{12}$ rlu) | Yield (%) | Purification Coefficient |
|---|---|---|---|---|---|---|---|---|
| Q-Sepharose FF Column | 25 | 8.0 | 200 | 2.34 | 2.93 | 5.85 | 82.9 | 2.20 |
| Ni-chelate FF Column | 26 | 1.75 | 45.5 | 1.82 | 10.40 | 4.73 | 67.1 | 7.82 |
| Ni-chelate FF Column | 4 | 2.40 | 9.6 | 2.50 | 10.42 | 1.00 | 100 | 7.83 |
| IgG-Sepharose 6FF Column | 10 | 0.78 | 7.8 | 1.03 | 13.21 | 1.03 | 103 | 9.93 |

Example 3

Purification of ZZ-AQ Fusion Protein

The conversion of ZZ-apoAQ fusion protein into ZZ-AQ fusion protein was carried out under the following conditions: The purified ZZ-apoAQ fusion protein obtained in Example 2 (1 mg) was dissolved in 5 mL of 50 mM Tris-HCL (pH 7.6) containing 10 mM DTT and 10 mM EDTA, following which a 24 μg of coelenterazine (a 1.2-fold equivalent) dissolved in ethanol was added and the mixture was left to stand one full day at 4° C. so as to effect conversion to ZZ-AQ fusion protein. The resulting ZZ-AQ fusion protein was concentrated using the Amicon Ultra-4 Centrifugal Filter Device (molecule weight cutoff, 10,000), then washed with 8 mL (four times using 2 mL each time) of 50 mM Tris-HCl (pH 7.6) containing 10 mM EDTA so as to remove excess coelenterazine. ZZ-AQ fusion protein was obtained at an activity recovery ratio of 95%.

Example 4

Figure 3:
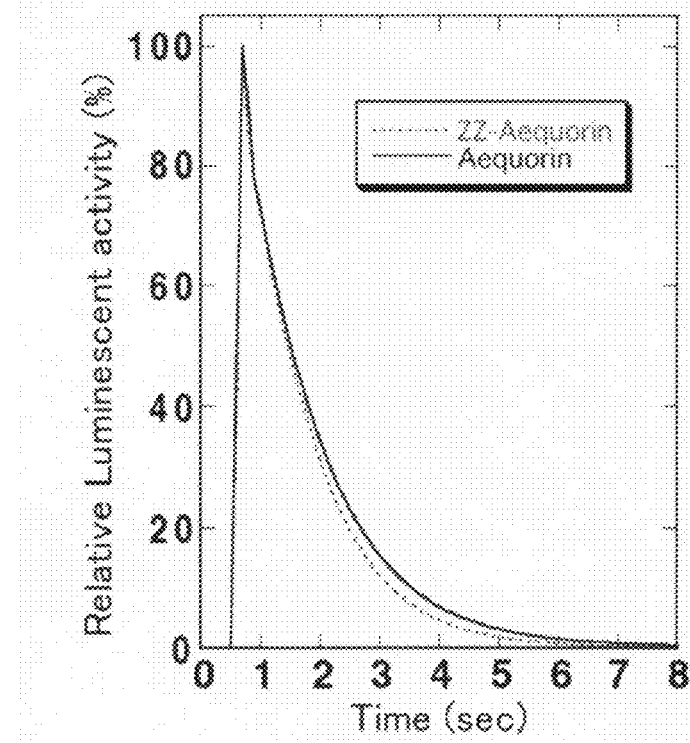
FIG. 3 shows the luminescence patterns obtained for the ZZ-aequorin fusion protein and for aequorin with the addition of calcium.

Comparison of Luminescent Activities of ZZ-AQ Fusion Protein and Native Aequorin To compare the luminescent performances of ZZ-AQ fusion protein and aequorin, their patterns of luminescence arising with calcium addition were compared. As shown in FIG. 3, the luminescence patterns for ZZ-AQ fusion protein and native aequorin, when compared in terms of their relative luminescent activities with respect to time, were similar. That is, in the ZZ-AQ fusion protein, the aequorin unit fused to the ZZ domain was found to exhibit an S/N ratio similar to that of native aequorin.

Example 5

Linearity of Protein Amount and Luminescence for ZZ-AQ Fusion Protein

Figure 4:
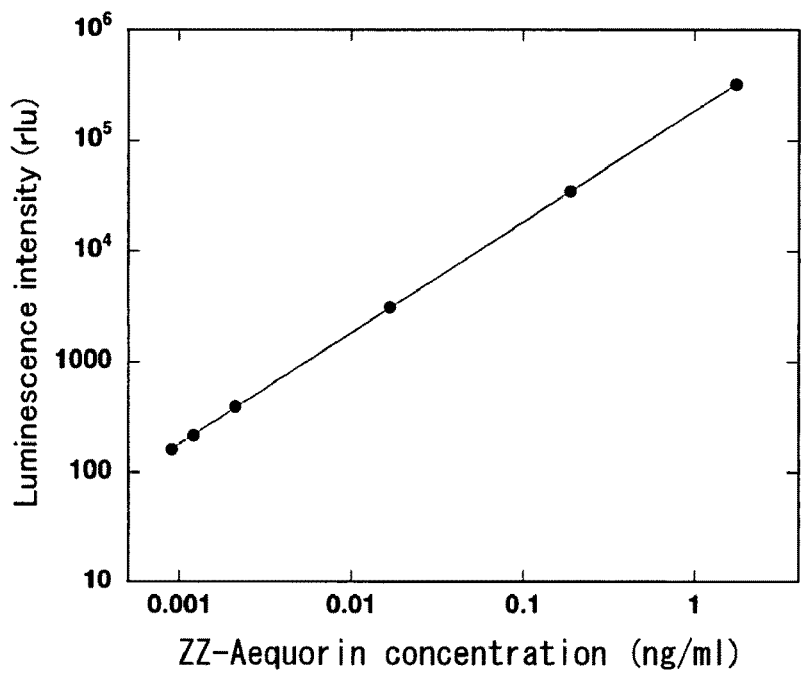
FIG. 4 shows the correlation between the concentration of the ZZ-aequorin fusion protein and its maximum luminescence intensity.

For the ZZ-AQ fusion protein to be used as a probe for detection, it must show linearity between the amount of protein and the luminescence. The concentration of ZZ-AQ fusion protein was set at from 1 picogram to 1 nanogram, 50 mM $CaCl_2$ 100 μl was poured in, and the luminescence was measured with a PSN AB2200 luminometer (Atto Corporation). The correlation between the maximum luminescent activity (Imax) and the protein concentration is shown in FIG. 4. A Linear correlation was observed between the luminescence intensity and the ZZ-AQ fusion protein. These results show that the amount of ZZ-AQ fusion protein can be quantitatively determined by measuring the luminescence.

Example 6

Methods for Detecting Human IgG Using ZZ-AQ Fusion Protein and Protein A-AQ Fusion Protein (1) Method for Detecting Human IgG Using ZZ-AQ Fusion Protein Human IgG (available from Experimental Immunology) was prepared to a concentration of 5 μg/mL by dilution with 50 mM carbonate buffer (pH 9.6). The resulting 5 μg/mL human IgG solution was dispensed onto a 96-microwell plate (Nunc, #437796) in amounts of 100 μl/well and left to stand overnight at 4° C., thereby coating the plate with human IgG. After standing, the human IgG solution was removed from the plate. Next, 2 mM Tris-HCl (pH 7.6) (referred to below as "TBS") containing 15 mM of NaCl was dispensed in amounts of 340 μl/well so as to wash the plate, following which the TBS was removed. The washing operation was repeated two more times to fully wash the plate. After washing, TBS containing 1% bovine serum albumin (available from Seikagaku Corporation; abbreviated below as "BSA") was dispensed in an amount of 300 μl/well, and left to stand at 37° C. for 1 hour. The above 1% BSA-containing TBS was then removed, and the plate was washed by dispensing 340 μl/well of TBS containing 0.05% Tween 20 (BioRad) and 2 mM EDTA (Wako Pure Chemical Industries) (which TBS solution is abbreviated below as "TBST-E"), after which the TBST-E was removed. The foregoing washing operation was repeated two more times to fully wash the plate. After washing, ZZ-AQ fusion protein (obtained in Example 3) prepared by dilution to concentrations of 0.2, 2, 20 and 200 ng/mL with TBS containing 0.1% BSA and 2 mM EDTA was dispensed in amounts of 100 μl/well and left to stand at 37° C. for 30 minutes. After standing, the ZZ-AQ fusion protein solution was removed. Next, the plate was washed by dispensing 340 μl/well of TBST-E, following which the TBST-E was removed. The washing operation was repeated two more times to fully wash the plate. After washing, 50 mM of Tris-HCl (pH 7.6) containing 50 mM of $CaCl_2$ was poured into the 96-microwell plate in amounts of 100 μl/well, and the luminescence intensity was measured for 5 seconds using a Centro LB960 microplate luminometer (Berthold). The luminescence intensity was rated in terms of the maximum luminescence intensity value (Imax).

(2) Human IgG Detection using Protein A-AQ Fusion Protein

Human IgG was prepared to a concentration of 5 μg/mL by dilution with a 50 mM carbonate buffer (pH 9.6). The resulting 5 μg/mL solution of human IgG was dispensed onto a 96-microwell plate (Nunc, #437796) in amounts of 100 μl/well and left to stand overnight at 4° C., thereby coating the plate with human IgG. After standing, the human IgG solution was removed from the plate. Next, the plate was washed by dispensing TBS in amounts of 340 μl/well, following which the TBS was removed. The washing operation was repeated two more times to fully wash the plate. After washing, TBS containing 1% BSA was dispensed to the plate in amounts of 300 μl/well and left to stand at 37° C. for 1 hour. After removal of the 1% BSA-containing TBS, the plate was washed by dispensing TBST-E in amounts of 340 μl/well, following which the TBST-E was removed. The washing operation was repeated two more times to fully wash the plate. After washing, Protein A-AQ fusion protein (obtained in Reference Example 1) prepared by dilution to concentrations of 0.2, 2, 20 and 200 ng/mL with TBS containing 0.1% BSA and 2 mM EDTA was dispensed in amounts of 100 μl/well, then left to stand at 37° C. for 30 minutes. After standing, the Protein A-AQ fusion protein solution was removed. Next, the plate was washed by dispensing 340 μl/well of TBST-E, following which the TBST-E was removed. The washing operation was repeated two more times to fully wash the plate. After washing, 50 mM Tris-HCl (pH 7.6) containing 50 mM of $CaCl_2$ was poured onto the plate in amounts of 100 μl/well, and the luminescence intensity was measured for 5 seconds using a Centro LB960 microplate luminometer (Berthold). The luminescence intensity was rated in terms of the maximum luminescence intensity value (Imax).

Figure 5:
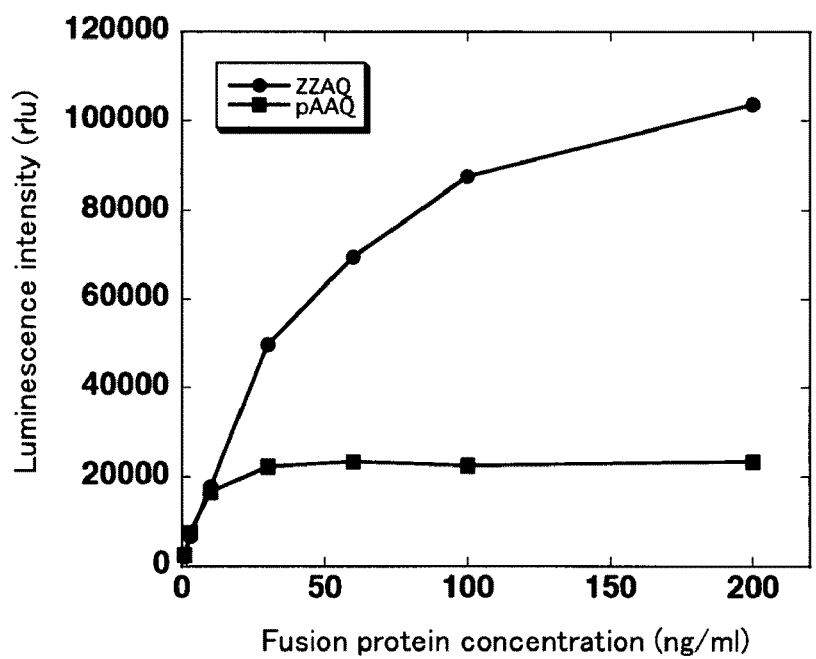
FIG. 5 shows the correlation between protein concentration and maximum luminescence intensity in a human IgG detection method using the ZZ-aequorin fusion protein and the protein A-aequorin fusion protein. "ZZAQ" stands for ZZ-aequorin fusion protein. "pAAQ" stands for Protein A-aequorin fusion protein.

Measurement results for the ZZ-AQ fusion protein and the Protein A-AQ fusion protein are shown in FIG. 5. It was confirmed that the luminescence intensity obtained with the Protein A-AQ fusion protein reached a plateau at a concentration of 10 ng/mL with Protein A-AQ fusion protein, whereas the luminescence intensity obtained with the ZZ-AQ fusion protein continued rising up to a concentration of 200 ng/mL. This data suggests that the ZZ-AQ fusion protein binds more strongly to IgG than does the Protein A-AQ fusion protein. Moreover, a comparison of the luminescence intensities also showed that the ZZ-AQ fusion protein has an IgG binding strength which is approximately five times higher than that of the Protein A-AQ fusion protein. It was clear from these results that the IgG detection sensitivity is higher when the ZZ-AQ fusion protein is used than when the Protein A-AQ fusion protein is used.

Example 7

IgG Detection Limit When ZZ-AQ Fusion Protein is Used

Figure 6:
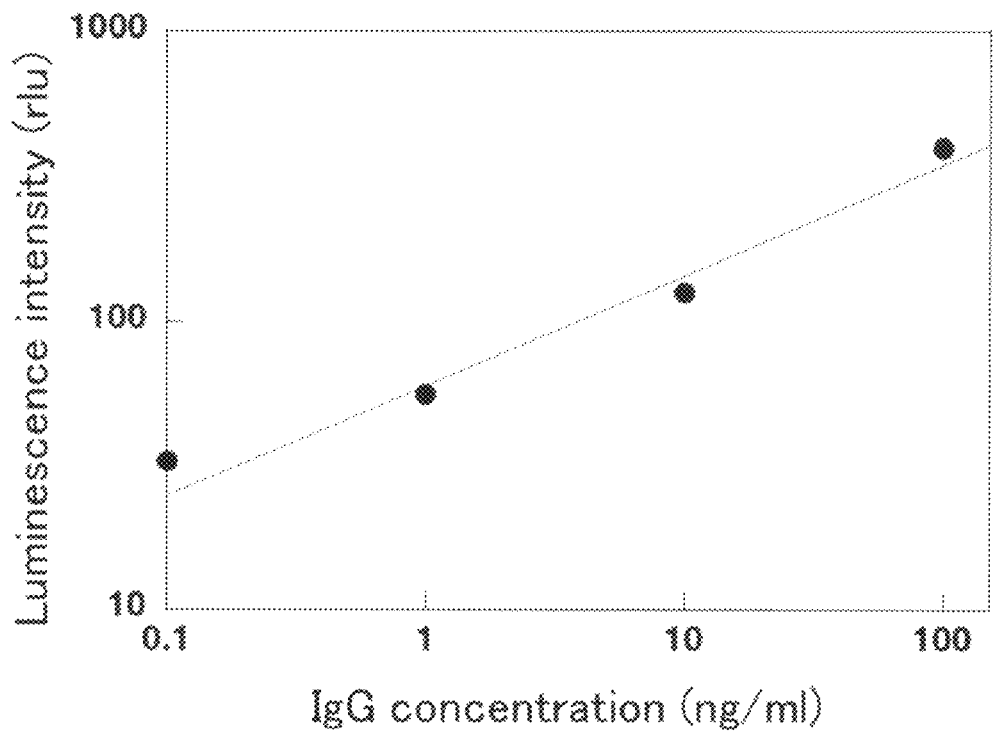
FIG. 6 shows the results of an IgG detection test in an IgG detection method using the ZZ-aequorin fusion protein.

In the method of detecting IgG with ZZ-AQ fusion protein of Example 6, the detection limit was measured using IgG solutions having concentrations ranging from 0.1 ng/mL to 100 ng/mL. As a result, judging from the linearity, the detection limit for IgG was found to be 0.1 ng/mL or less (FIG. 6). This data indicates that the minimum concentration of ZZ-AQ fusion protein at which IgG can be measured is 1 ng/mL or less per assay. From the above results, it was thus found that with the use of the ZZ-AQ fusion protein, IgG can be detected at a sensitivity that is from 10 to 20 times greater or more than with the use of a fusion protein of Protein A and aequorin (minimum measurable concentration of IgG, 20 ng/mL; Biochem. Biophys. Res. Commun., 171, 169-174 (1990)) or the use of a fusion protein of the ZZ domain and obelin (minimum measurable concentration of IgG, 10 ng/mL; *Biochem. Biophys. Res. Commun.*, 219, 475-479 (1996)).

Example 8

Method of Assaying Biotin by the Competition Method Using ZZ-AQ Fusion Protein

Figure 7:
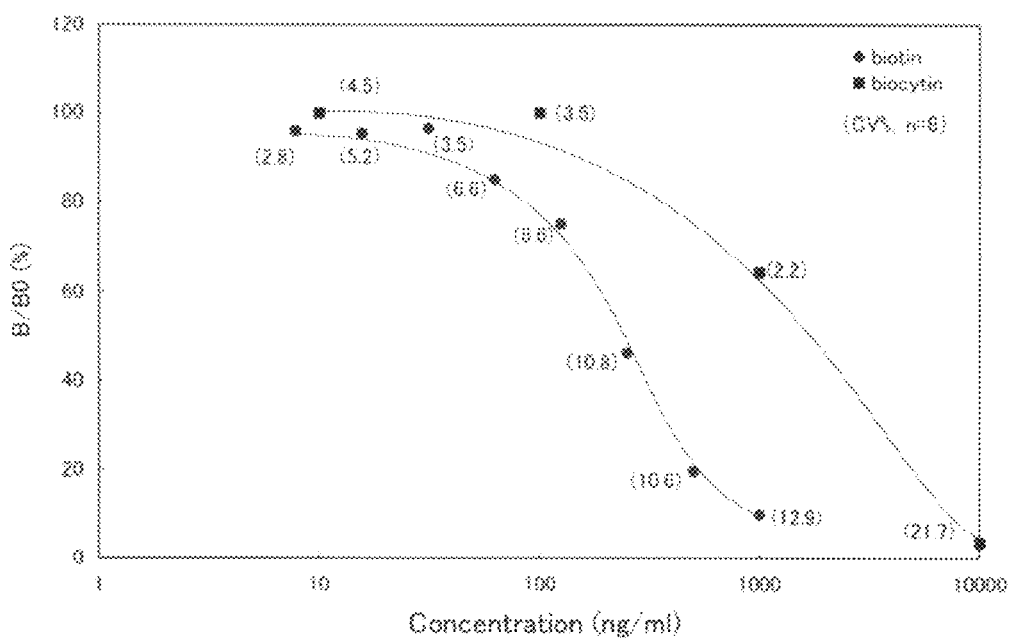
FIG. 7 shows the results of biotin and biocytin assays by the competition method using the ZZ-aequorin fusion protein.

Biotinylated BSA (Sigma) was prepared to a concentration of 5 μg/mL by dilution with a 50 mM carbonate buffer (pH 9.6). The resulting 5 μg/mL biotinylated BSA solution was dispensed onto a 96-microwell plate (Nunc, #437796) in amounts of 100 μL/well and left to stand overnight at 4° C., thereby coating the plate with biotinylated BSA. After standing, the biotinylated BSA solution was removed from the plate. Next, the plate was washed by dispensing TBS thereon in amounts of 340 μl/well, following which the TBS was removed from the plate. The washing operation was repeated two more times. After washing, TBS containing 1% BSA was dispensed to the plate in amounts of 300 μl/well and left to stand at 37° C. for 1 hour. The TBS containing 1% BSA was then removed from the plate. The plate was then washed by dispensing TBST-E thereon in amounts of 340 μl/well, after which the TBST-E was removed. The washing operation was repeated two more times. After washing, 50 μl of a biotin solution prepared by dilution to a concentration of from 8 ng/mL to 1,000 ng/mL with TBS containing 0.1% BSA and 2 mM EDTA or 50 μl of a biocytin (a biotin analog) solution likewise prepared by dilution to a concentration of from 10 ng/mL to 10,000 ng/mL, and 50 μl of an anti-biotin monoclonal antibody solution (Sigma; used as a 12,000-fold dilution) were successively added, then left to stand at 25° C. for 2 hours. After standing, the reaction solution was removed and the plate was washed by dispensing 340 μl/well of TBST-E, following which the TBST-E was removed. The washing operation was repeated two more times. Next, 100 μl of the ZZ-AQ fusion protein (250 ng/mL) was added to the plate, and left to stand at 25° C. for 1 hour. After standing, the reaction solution was removed and the plate was washed by dispensing 340 μl/well of TBST-E, following which the TBST-E was removed. The plate was washed by repeating the foregoing washing operation two more times. Next, 100 μl/well of 50 mM Tris-HCl (pH 7.6) containing 50 mM of $CaCl_2$ was poured into the washed plate and the luminescence intensity was measured for 5 seconds with a Centro LB960 plate luminometer. The luminescent intensity was evaluated as the maximum luminescent intensity value (Imax). The results are shown in FIG. 7. These results indicate that the anti-biotin monoclonal antibody which bonded to the biotin or biocytin was quantitatively detected by the ZZ-AQ fusion protein. That is, it was demonstrated that free biotin or free biocytin can be quantitatively determined by using competitive reactions, between free biotin (or free biocytin) and immobilized biotin, for binding to the anti-biotin monoclonal antibody.

INDUSTRIAL APPLICABILITY

The fusion protein of the invention, when brought into contact with the light-emitting substrate coelenterazine, is capable of easily forming a holoprotein containing the inventive fusion protein and a peroxide of coelenterazine. The holoprotein of the invention, when in the presence of coelenterazine and oxygen, exists in the state of a complex that has formed between the inventive fusion protein and a peroxide of coelenterazine. When a calcium ion bonds to the complex, light is momentarily emitted. Therefore, the fusion protein and the holoprotein of the invention can be advantageously employed for detecting and measuring calcium ions.

Moreover, the fusion protein of the invention has a high ability to bind to IgG. Furthermore, as noted above, holoproteins, which are composed of the fusion protein of the invention and a peroxide of the light-emitting substrate coelenterazine, are capable of emitting light under the action of calcium ions. Therefore, the fusion protein and holoprotein of the invention can be advantageously employed for detecting IgG.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A fusion protein comprising:
   (1) a first region selected from the group of:
      (a) a region having the amino acid sequence of SEQ ID NO: 1;
      (b) a region having variants of the amino acid sequence of SEQ ID NO: 1, wherein said variants have from one to eight deleted, substituted, inserted and/or added amino acids, and which has the ability to bind to the Fc region of IgG; and
      (c) a region which has an amino acid sequence that is at least approximately 94% identical to the amino acid sequence of SEQ ID NO: 1, and which has the ability to bind to the Fc region of IgG; and
   (2) a second region selected from the group of:
      (d) a region having the amino acid sequence of SEQ ID NO: 3;
      (e) a region having variants of the amino acid sequence of SEQ ID NO: 3, wherein said variants have from one to eight deleted, substituted, inserted and/or added amino acids, and which has the ability to bind to a peroxide of coelenterazine or a peroxide of a coelenterazine derivative so as to form a holoprotein that emits light under the action of a calcium ion; and
      (f) a region which has an amino acid sequence that is at least approximately 95% identical to the amino acid sequence of SEQ ID NO: 3, and which has the ability to bind to a peroxide of coelenterazine or a peroxide of a coelenterazine derivative so as to form a holoprotein that emits light under the action of a calcium ion,
   wherein the fusion protein has a minimum IgG-detection sensitivity of 1 ng/ml.

2. The fusion protein of claim 1, wherein
   (1) the first region is selected from the group of:
      (a) a region having the amino acid sequence of SEQ ID NO: 1,
      (b) a region having variants of the amino acid sequence of SEQ ID NO: 1, wherein said variants have from one to three deleted, substituted, inserted and/or added amino acids, and which has the ability to bind to the Fc region of IgG, and
      (c) a region which has an amino acid sequence that is at least approximately 98% identical to the amino acid sequence of SEQ ID NO: 1, and which has the ability to bind to the Fc region of IgG; and
   (2) the second region is selected from the group of:
      (d) a region having the amino acid sequence of SEQ ID NO: 3,
      (e) a region having variants of the amino acid sequence of SEQ ID NO: 3, wherein said variants have from one to four deleted, substituted, inserted and/or added amino acids, and which has the ability to bind to a peroxide of coelenterazine or a peroxide of a coelenterazine derivative so as to form a holoprotein that emits light under the action of a calcium ion, and
      (f) a region which has an amino acid sequence that is at least approximately 98% identical to the amino acid sequence of SEQ ID NO: 3, and which has the ability to bind to a peroxide of coelenterazine or a peroxide of a coelenterazine derivative so as to form a holoprotein that emits light under the action of a calcium ion.

3. A fusion protein comprising:
   (1) a region having a first amino acid sequence of SEQ ID NO: 1, and
   (2) a region having a second amino acid sequence of SEQ ID NO: 3,
   wherein the fusion protein has a minimum IgG-detection sensitivity of 1 ng/ml.

4. The fusion protein according to claim 1, further comprising at least one amino acid sequence for enhancing at least one of translation and purification.

5. A fusion protein having the amino acid sequence of SEQ ID NO: 5.

6. A holoprotein comprising the fusion protein of claim 1 and a peroxide of coelenterazine or a peroxide of a coelenterazine derivative.

7. A kit comprising the fusion protein of claim 1.

8. An immunoassay kit comprising the fusion protein of claim 1.

9. A method for detecting or assaying calcium ions, comprising using the fusion protein of claim 1.

10. An immunoassay method, comprising using the fusion protein of claim 1.

11. A kit comprising the holoprotein of claim 6.

12. An immunoassay kit comprising the holoprotein of claim 6.

13. A method for detecting or assaying calcium ions, comprising using the holoprotein of claim 6.

14. An immunoassay method, comprising using the holoprotein of claim 6.

15. A holoprotein comprising the fusion protein of claim 2 and a peroxide of coelenterazine or a peroxide of a coelenterazine derivative.

16. A holoprotein comprising the fusion protein of claim 3 and a peroxide of coelenterazine or a peroxide of a coelenterazine derivative.

17. A holoprotein comprising the fusion protein of claim 4 and a peroxide of coelenterazine or a peroxide of a coelenterazine derivative.

18. A holoprotein comprising the fusion protein of claim 5 and a peroxide of coelenterazine or a peroxide of a coelenterazine derivative.

* * * * *